(12) United States Patent
Zysman-Colman et al.

US010593893B2

(10) Patent No.: US 10,593,893 B2
(45) Date of Patent: Mar. 17, 2020

(54) LIGHT EMITTING DEVICES AND COMPOUDS

(71) Applicant: UNIVERSITY COURT OF THE UNIVERSITY OF ST ANDREWS, St Andrews (GB)

(72) Inventors: Eli Zysman-Colman, Fife (GB); Michael Yin Wong, Fife (GB)

(73) Assignee: UNIVERSITY COURT OF THE UNIVERSITY OF ST ANDREWS, St Andrews (GB)

(*) Notice: Subject to any disclaimer, the term of this patent is extended or adjusted under 35 U.S.C. 154(b) by 0 days.

(21) Appl. No.: 15/569,669

(22) PCT Filed: Dec. 29, 2015

(86) PCT No.: PCT/GB2015/054171
§ 371 (c)(1),
(2) Date: Oct. 26, 2017

(87) PCT Pub. No.: WO2016/174377
PCT Pub. Date: Nov. 3, 2016

(65) Prior Publication Data
US 2018/0123052 A1 May 3, 2018
US 2020/0028093 A2 Jan. 23, 2020

(30) Foreign Application Priority Data
Apr. 29, 2015 (GB) .................................. 1507340.6

(51) Int. Cl.
| | | |
|---|---|---|
| H01L 51/00 | (2006.01) | |
| C07D 417/10 | (2006.01) | |
| C09K 11/06 | (2006.01) | |
| C07D 413/10 | (2006.01) | |
| C07F 9/572 | (2006.01) | |
| C07D 265/38 | (2006.01) | |
| C07D 279/22 | (2006.01) | |
| C07D 413/14 | (2006.01) | |
| H01L 51/50 | (2006.01) | |

(52) U.S. Cl.
CPC ........ *H01L 51/0072* (2013.01); *C07D 265/38* (2013.01); *C07D 279/22* (2013.01); *C07D 413/10* (2013.01); *C07D 413/14* (2013.01); *C07D 417/10* (2013.01); *C07F 9/572* (2013.01); *C07F 9/5728* (2013.01); *C09K 11/06* (2013.01); *H01L 51/007* (2013.01); *H01L 51/0071* (2013.01); *C09K 2211/1007* (2013.01); *C09K 2211/1018* (2013.01); *C09K 2211/1029* (2013.01); *C09K 2211/1033* (2013.01); *C09K 2211/1037* (2013.01); *H01L 51/5012* (2013.01); *H01L 51/5016* (2013.01); *H01L 51/5032* (2013.01)

(58) Field of Classification Search
CPC ............... H01L 51/0072; H01L 51/007; H01L 51/0071; C07D 265/38; C07D 279/22; C07D 413/10; C07D 413/14; C07D 417/10; C07F 9/572; C07F 9/5728; C09K 11/06
See application file for complete search history.

(56) References Cited

U.S. PATENT DOCUMENTS

| | | |
|---|---|---|
| 2010/0280083 A1 | 11/2010 | Ishikawa et al. |
| 2010/0305142 A1 | 12/2010 | Klein et al. |
| 2014/0174537 A1 | 6/2014 | Fadhel |
| 2016/0093812 A1 | 3/2016 | Stoessel et al. |
| 2016/0181545 A1 | 6/2016 | Stoessel et al. |
| 2017/0244049 A1* | 8/2017 | Aspuru-Guzik ....... C09K 11/06 |

FOREIGN PATENT DOCUMENTS

| | | | | |
|---|---|---|---|---|
| JP | 07109453 A | * | 4/1995 | |
| JP | 2005060382 A | * | 3/2005 | |
| JP | 2010506863 A | | 3/2010 | |
| JP | 2012051884 A | | 3/2012 | |
| JP | 2014520394 A | | 8/2014 | |
| WO | 2009081891 A1 | | 7/2009 | |
| WO | WO-2012168358 A1 | * | 12/2012 | ........... C07D 471/16 |
| WO | 2013183327 A1 | | 12/2013 | |
| WO | 2014166586 A1 | | 10/2014 | |
| WO | 2014194971 A1 | | 12/2014 | |
| WO | 2015022835 A1 | | 2/2015 | |
| WO | WO-2015022835 A1 | * | 2/2015 | ........... C07D 401/14 |
| WO | 2015175678 A1 | | 11/2015 | |
| WO | 2016174377 A1 | | 11/2016 | |

OTHER PUBLICATIONS

M. Yabe et al., JP 2005060382, English Language Machine Translation (2005) (Year: 2005).*
English Language Machine Translation of WO 2015/022835 (2015) (Year: 2015).*
G. F. Manbeck et al., 49 Inorganic Chemistry, 2834-2843 (2010) (Year: 2010).*
March's Advanced Organic Chemistry: Reactions, Mechanisms, and Structure, Seventh Edition. (2013) (Year: 2013).*
V. K. Olkhovik et al., ARKIVOC, 69-93 (2008) (Year: 2008).*
Melhuish, W. H.; "Quantum Efficiencies of Fluorescence of Organic Substances: Effect of Solvent and Concentration of the Fluorescent Solute", Journal of Physical Chemistry, Feb. 1961, vol. 65, pp. 229-235.

(Continued)

*Primary Examiner* — Alexander R Pagano
(74) *Attorney, Agent, or Firm* — Christopher J. Knors; Moore & Van Allen PLLC

(57) ABSTRACT

Thermally Activated Delayed Fluorescence (TADF) compounds wherein two aromatic heterocyclic moieties are provided as acceptor groups, spaced apart from two donor moieties by an aromatic spacer ring, are described. Charged organic TADF species having a similar structure are also described. The TADF compounds and charged organic TADF species may be employed as emitter material in light emitting devices such as OLEDs and LEECs. Also described TADF compounds wherein at least one donor moiety is substituted by at least one substituent that is a phosphine oxide or a phosphine sulphide.

14 Claims, 2 Drawing Sheets

(56) References Cited

OTHER PUBLICATIONS

Crosby, G. A., et al; "The Measurement of Photoluminescence Quantum Yields. A Review", The Journal of Physical Chemistry, Apr. 1971, vol. 75, No. 8, pp. 991-1024.

Martin, Colin J. et al: "Oxidative Bond Formation in Dithienyl Polyphenylenes: Optical and Electrochemical Consequences", European Journal of Organic Chemistry, 2011, vol. 2011 No. 19, pp. 3491-3499.

Zheng, Yonghao, et al.; "Bipolar Molecules with High Triplet Energies: Synthesis, Photophysical, and Structural Properties", The Journal of Organic Chemistry, 2011, vol. 76, pp. 8300-8310.

Wong, Michael Y., et al; "Light-Emitting Electrochemical Cells and Solution-Processed Organic Light-Emitting Diodes Using Small Molecule Organic Thermally Activated Delayed Fluorescence Emitters", Chemistry of Materials, Jul. 14, 2015, vol. 27 No. 19, pp. 6535-6542.

Mehes, Gabor, et al; "Enhanced Electroluminescence Efficiency in a Spiro-Acridine Derivative through Thermally Activated Delayed Fluorescence", Angewandte Chemie, International Edition, 2012, vol. 51, pp. 11311-11315.

Zhang, Qisheng, et al; "Design of Efficient Thermally Activated Delayed Fluorescence Materials for Pure Blue Organic Light Emitting Diodes". Journal of the American Chemical Society, 2012, vol. 134, pp. 14706-14709.

Yu, W., et al; "I2-Mediated Oxidative C—O Bond Formation for the Synthesis of 1,3,4-Oxadiazoles from Aldehydes and Hydrazides", The Journal of Organic Chemistry, 2013, vol. 78, pp. 10337-10343.

Lee, S. Y., et al; "Luminous Butterflies: Efficient Exciton Harvesting by Benzophenone Derivatives for Full-Color Delayed Fluorescence OLEDS", Angewandte Chemie, International Edition, 2014, vol. 53, pp. 6402-6406.

UK Patent Office; Search Report for UK Application No. GB1507340.6 dated Feb. 2, 2016, 5 pages.

Sandanayaka, Atula S.D. et al; "Exciton Quenching Behavior of Thermally Activated Delayed Fluorescence Molecules by Charge Carriers", The Journal of Physical Chemistry, 2015, vol. 119, pp. 7631-7636.

Nishide, Jun-Ichi, et al; "High-efficiency white organic light-emitting diodes using thermally activated delayed fluorescence", Applied Physics Letters, 2014, vol. 104 issue 23, pp. 233304-1-233304-5.

Ishimatsu, Ryoichi, et al; "Electrogenerated Chemiluminescence of Donor-Acceptor Molecules with Thermally Activated Delayed Fluorescence", Angewandte Chemie, International Edition, 2014, vol. 53 part 27, pp. 6993-6996.

Nakanotani, Hajime, et al; "High-efficiency organic light-emitting diodes with fluorescent emitters", Nature Communications, 2014, DOI: 10.1038/ncomms5016, pp. 1-7.

Reineke, Sebastian; "Phosphorescence meets its match", Nature Photonics, Apr. 2014, vol. 8, pp. 269-270.

Joyama, Hiroki, et al; "Highly efficient organic light-emitting diodes from delayed fluorescence", Nature, Dec. 2012, vol. 492 No. 7428, pp. 234-238.

WIPO; Written Opinion and International Search Report for International Application No. PCT/GB2015/054171 dated Jun. 20, 2016, 15 pages.

Zhang, Qisheng, et al; "Efficient blue organic light-emitting diodes employing thermally activated delayed fluorescence", Nature Photonics, Apr. 2014, vol. 8, pp. 326-332.

Zhang, Jing, et al; "Efficient light-emitting Electrochemical Cells (LECs) Based on Ionic Iridium(III) Complexes with 1,3,4-Oxadiazole Ligands", Advanced Functional Materials Journal, 2013, vol. 23, pp. 4667-4677.

Juricek, Michal, et al.; "The trisubstituted-triazole approach to extended functional naphthalocyanines," Journal of Porphyrins and Phthalocyanines, 2011, pp. 898-907, vol. 15.

Chinese Patent Office; Office Action for Chinese Patent Application No. 2017-556849 dated Dec. 2, 2019, 10 Pages.

\* cited by examiner

LIGHT EMITTING DEVICES AND COMPOUDS

CROSS-REFERENCE TO RELATED APPLICATIONS

This application is a 35 U.S.C. § 371 National Stage Application of International Application No. PCT/GB2015/054171, filed Dec. 29, 2015, which claims the benefit of UK Application No. 1507340.6 filed on Apr. 29, 2015, the entirety of each of which is incorporated herein by reference.

FIELD OF THE INVENTION

The present invention is directed to the provision of Thermally Activated Delayed Fluorescence (TADF) compounds for use in OLEDs or other light emitting devices.

BACKGROUND TO THE INVENTION

Organic Light Emitting Diodes (OLEDs) have come to the fore as the state-of-the-art technology for visual displays and lighting. OLEDs are desirable as they are light-weight, flexible, provide better contrast and possess large viewing angle. OLEDs are also more power efficient than traditional lighting sources and thus their wide adoption can alleviate significantly the strain on current energy demand because lighting alone constitutes about 20% of energy consumption worldwide.

The "first generation" OLEDs were based on organic fluorescent emitters whose efficiency was intrinsically capped at 25% due to only being able to recruit singlet excitons. The "second generation" OLEDs employed organometallic phosphorescent emitters, which harvest both singlet and triplet excitons for emission due to the enhanced intersystem crossing (ISC) mediated by the large spin-orbit coupling of heavy metals such as iridium(III) and platinum (II). Despite their highly desirable performance characteristics, the rarity of these metals, their high cost and their toxicity are important detracting features that inhibit large-scale, worldwide adoption of OLED technology.

The "third generation" OLEDs were recently first reported by Adachi and co-workers. His group demonstrated how small organic molecules, emitting via a thermally activated delayed fluorescence (TADF) mechanism, could be integrated into OLEDs and exhibit very high efficiencies as, like with phosphorescent emitters, both singlet and triplet excitons are recruited for emission (Reference 1). Thus, TADF-based OLEDs address the key detracting features endemic to "second generation" OLEDs while retaining their advantages (Reference 2).

The principle of TADF relies on a small energy gap between the lowest singlet and triplet excited states ($\Delta E_{ST}$). Under these conditions, the electrons in the triplet state can return to the singlet state by reverse intersystem crossing (RISC) using thermal energy, followed by radiative fluorescence (Reference 1a). The small $\Delta E_{ST}$ is realized by spatial separation between HOMO and LUMO to minimize the electronic repulsion between these orbitals. A large number of organic TADF emitters have been reported to date. They can make use of donor and acceptor moieties of various types within the molecule to achieve the desired small energy gap between the lowest singlet and triplet excited states ($\Delta E_{ST}$). The majority of these molecules are based on a twisted intramolecular charge transfer (TICT) design in which the donor and acceptor moieties are designed to be nearly orthogonal to each other (References 1a, 1c and 3).

Despite the progress made there is a need to provide improved and alternative compounds for use in display and lighting uses, such as in organic light emitting diodes (OLEDs) and light emitting electrochemical cells (LEECs).

DESCRIPTION OF THE INVENTION

According to a first aspect, the present invention provides a compound according to formula I:

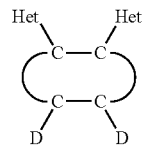

I wherein the ring II:

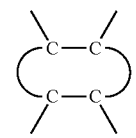

II represents an aromatic spacer ring with each Het bonded to adjacent carbon atoms and each moiety D bonded to adjacent carbon atoms, and
wherein each Het is an aromatic heterocyclic moiety and each D is a donor moiety.

The compound according to formula I exhibits TADF behaviour. The aromatic heterocyclic groups Het act as acceptor groups and the donor moieties D act as donor groups. The spatial separation of Het and D by the ring II provides segregation of the HOMO (centred on donors D) and LUMO (centred on acceptors Het) that provides efficient TADF behaviour.

The ring II may be a benzene ring and thus the compound of the invention may be according to formula III:

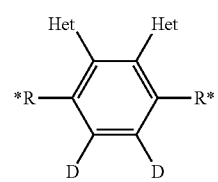

III wherein D and Het have the same meaning as before. R* may be, independently for each occurrence, selected from the group consisting of —H, alkyl, aryl or heteroaryl (for example substituted or unsubstituted C1-C20 or even C1-C10). The aromatic heterocyclic moieties Het may be, independently for each occurrence selected from the group consisting of:

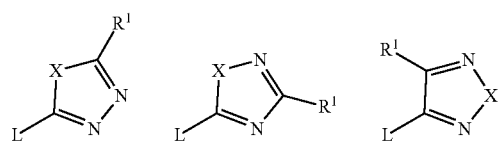

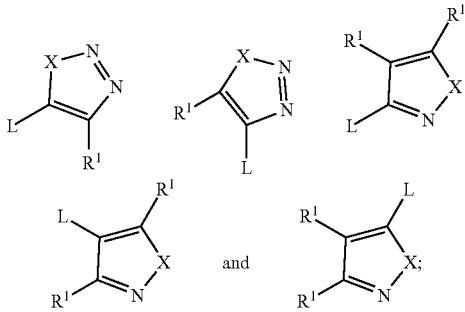

wherein -L represents the bonding position to ring II or III, X represents O, S or $NR^2$ and groups $R^2$ are, independently for each occurrence, selected from the group consisting of —H, substituted or unsubstituted primary, secondary or tertiary alkyl, that may be cyclic and may be unsaturated (for example C1-C10 or even C1-C4); substituted or unsubstituted aryl or heteroaryl;

wherein groups $R^1$ are, independently for each occurrence, selected from the group consisting of —H, substituted or unsubstituted primary, secondary or tertiary alkyl, that may be cyclic and may be unsaturated (for example C1-C10 or even C1-C4); substituted or unsubstituted aryl or heteroaryl, —$CF_3$, —OMe, —$SF_5$, —$NO_2$, halo (e.g. fluoro, chloro, bromo and iodo), aryl, aryl hydroxy, amino, alkoxy, alkylthio, carboxy, cyano, thio, formyl, ester, acyl, thioacyl, amido, sulfonamido, carbamate, phosphine oxide, phosphine sulphide and the like.

Where the group $R^1$ is amino it may be —$NH_2$, —NHR or —$NR_2$, where the substituents R on the nitrogen may be alkyl, aryl or heteroaryl (for example substituted or unsubstituted C1-C20 or even C1-C10).

Where the groups $R^*$, $R^1$ or $R^2$ (or any other groups such as R, and $R^3$ to $R^9$ provided in structures discussed herein), are described as substituted they may be independently substituted for each occurrence. For example once, twice, or three times, e.g. once, i.e. formally replacing one or more hydrogen atoms with substituents such as halo (e.g. fluoro, chloro, bromo and iodo), —$SF_5$, —$CF_3$, —OMe, —$NO_2$, substituted or unsubstituted primary, secondary or tertiary alkyl, that may be cyclic and may be unsaturated (for example C1-C10 or even C1-C4); substituted or unsubstituted aryl or heteroaryl, aryl hydroxy, amino, alkoxy, alkylthio, carboxy, cyano, thio, formyl, ester, acyl, thioacyl, amido, sulfonamido, carbamate and the like. Where the substituent is amino it may be $NH_2$, NHR or $NR_2$, where the substituents R on the nitrogen may be alkyl, aryl or heteroaryl (for example substituted or unsubstituted C1-C20 or even C1-C10).

By aryl is meant herein a radical formed formally by abstraction of a hydrogen atom from an aromatic compound. As known to those skilled in the art, heteroaryl moieties are a subset of aryl moieties that comprise one or more heteroatoms, typically O, N or S, in place of one or more carbon atoms and any hydrogen atoms attached thereto. Exemplary aryl substituents, for example, include phenyl or naphthyl that may be substituted. Exemplary heteroaryl substituents, for example, include pyridinyl, furanyl, pyrrolyl and pyrimidinyl.

Further examples of heteroaromatic rings include pyridazinyl (in which 2 nitrogen atoms are adjacent in an aromatic 6-membered ring); pyrazinyl (in which 2 nitrogens are 1,4-disposed in a 6-membered aromatic ring); pyrimidinyl (in which 2 nitrogen atoms are 1,3-disposed in a 6-membered aromatic ring); or 1,3,5-triazinyl (in which 3 nitrogen atoms are 1,3,5-disposed in a 6-membered aromatic ring).

Where the group $R^*$, $R^1$ or $R^2$ (or any of the groups R, $R^3$ to $R^9$ provided in structures discussed herein), includes one or more rings they may be cycloalkyl they may be for example cyclohexyl or cyclopentyl rings. The cyclohexyl or cyclopentyl groups if present may be saturated or unsaturated and may be substituted as described above.

Examples of aromatic heterocyclic moieties Het include 1,3,4 oxadiazoles:

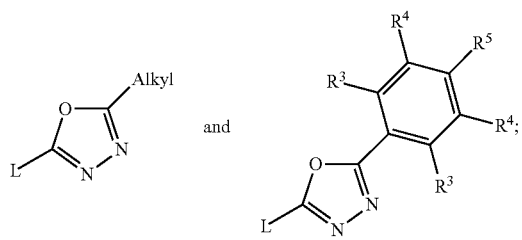

wherein -L represents the bonding position to ring II or III;

—Alkyl represents a substituted or unsubstituted primary, secondary or tertiary alkyl, that may be cyclic and may be unsaturated (for example C1-C10 or even C1-C4); and wherein groups $R^3$, $R^4$ and $R^5$ are, independently for each occurrence selected from the group consisting of:

—H, substituted or unsubstituted primary, secondary or tertiary alkyl, that may be cyclic and may be unsaturated (for example C1-C10 or even C1-C4); substituted or unsubstituted aryl or heteroaryl, —$CF_3$, —OMe, —$SF_5$, —$NO_2$, halo (e.g. fluoro, chloro, bromo and iodo), aryl, aryl hydroxy, amino, alkoxy, alkylthio, carboxy, cyano, thio, formyl, ester, acyl, thioacyl, amido, sulfonamido, carbamate, phosphine oxide, phosphine sulphide and the like.

D are donor moieties that may take several different forms as known in the field of TADF compounds. They may be the same or different for each occurrence For example donor moieties D may be:

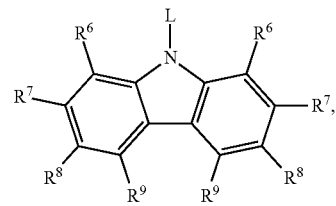

wherein -L represents the bonding position to ring II or III; each group $R^6$, $R^7$, $R^8$ and $R^9$ is, independently for each occurrence, selected from the group consisting of —H, substituted or unsubstituted primary, secondary or tertiary alkyl, that may be cyclic and may be unsaturated (for example C1-C10 or even C1-C4); substituted or unsubstituted aryl or heteroaryl, —$CF_3$, —OMe, —$SF_5$, —$NO_2$, halo (e.g. fluoro, chloro, bromo and iodo), aryl, aryl hydroxy, amino, alkoxy, alkylthio, carboxy, cyano, thio, formyl, ester, acyl, thioacyl, amido, sulfonamido, carbamate, phosphine oxide, phosphine sulphide and the like.

Where the group (one or more of $R^6$, $R^7$, $R^8$ and $R^9$) is amino it may be —$NH_2$, —NHR or —$NR_2$, where the substituents R on the nitrogen may be substituted or unsubstituted alkyl, aryl or heteroaryl (for example substituted or unsubstituted C1-C20 or even C1-C10).

Where the group (one or more of $R^6$, $R^7$, $R^8$ and $R^9$) is phosphine oxide or phosphine sulphide it may be selected from the group consisting of:

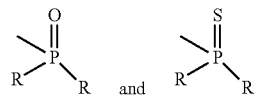

where the substituents R on the phosphorus may be substituted or unsubstituted alkyl, aryl or heteroaryl (for example substituted or unsubstituted C1-C20 or even C1-C10).

The phosphine oxide or phosphine sulphide substituent may be para to the nitrogen of the carbazole structure i.e. one or both of $R^8$ may be a phosphine oxide or phosphine sulphide substituent. Conveniently where both $R^8$ are a phosphine oxide or phosphine sulphide substituent they may be the same. The phosphine oxide or phosphine sulphide substituent may have phenyl or substituted phenyl groups R on the phosphorus.

Thus substituents:

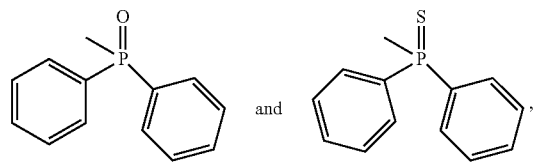

or substituents where one or both phenyl groups are substituted, are contemplated for donor moieties D.

Phosphine oxide or phosphine sulphide may be used as acceptor moieties, or part of acceptor moieties (substituents on acceptor moieties) in the structure of a TADF molecule, such as the TADF compounds described herein.

Where used as a substituent on a donor moiety D as described herein, phosphine oxide or phosphine sulphide acts to moderate the character of the donor and can therefore alter the photo physical behaviour of a TADF compound, for example resulting in a change in colour and or intensity of emission. The use of phosphine oxide or phosphine sulphide as a substituent on a donor moiety D of a TADF compound, such as the compounds described herein constitutes another aspect of the invention.

More generally moieties D may also be selected from:

A
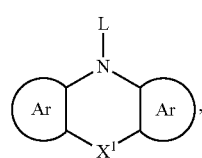

B
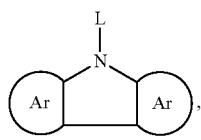

C
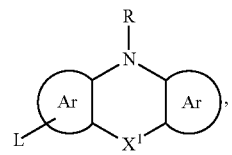

D
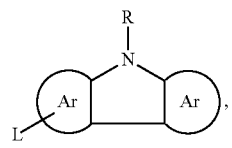

E
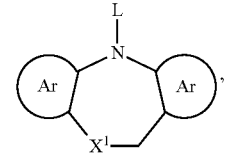

F
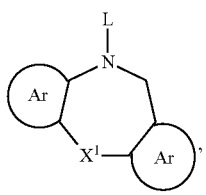

G
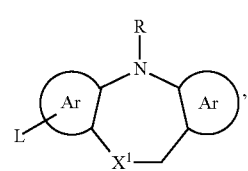

H
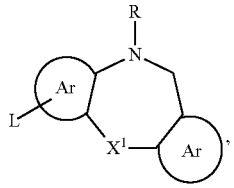

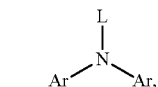

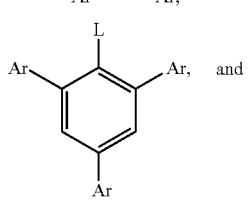

and

-continued

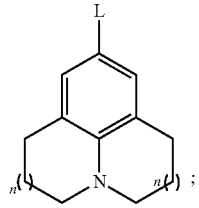

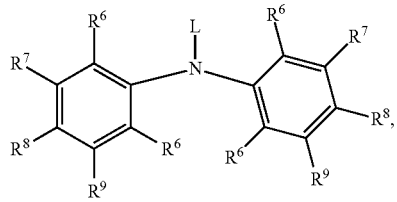

wherein -L represents the bonding position to ring II or III, that is para to the nitrogen in structures C, D, G and H;

$X^1$ is selected from the group consisting of O, S, NR, SiR$_2$, PR and CR$_2$, wherein each R is independently selected from the group consisting of —H, alkyl, aryl or heteroaryl (for example substituted or unsubstituted C1-C20 or even C1-C10);

each Ar is independently for each occurrence selected from the group consisting of substituted or unsubstituted aryl or heteroaryl; and

represents, independently for each occurrence a substituted or unsubstituted aryl or heteroaryl ring fused to the central ring of structures A B, C, D, E or F for example a five or a six membered substituted or unsubstituted aryl or heteroaryl ring; and n( ) indicates the optional presence of saturated —CH$_2$— groups in the rings annelated to the benzene ring, wherein n is independently for each occurrence, 0, 1, or 2.

Substituents on —Ar and

where present can include phosphine oxide or phosphine sulphide, as discussed above, to moderate the donor properties.

Thus moieties D may be selected from:

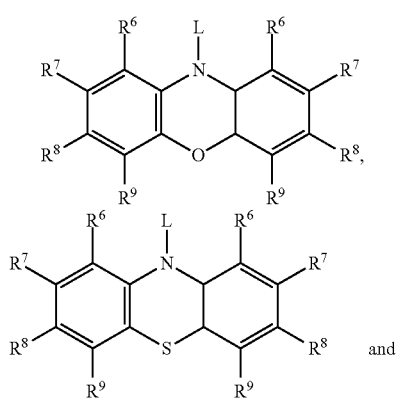

wherein the groups $R^6$, $R^7$, $R^8$ and $R^9$ may take the same meaning as before.

The saturated rings annelated to the benzene ring in the structure:

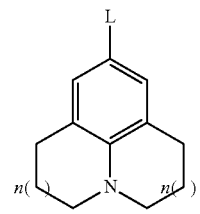

may be five six or seven membered rings. Typically they may be six membered, i.e. the juliolidine structure, where n is 1:

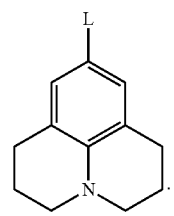

Exemplary compounds include structures IV, V and VI, below, where the moieties Het are 1,3,4 oxadiazoles and the donor moieties D are carbazole:

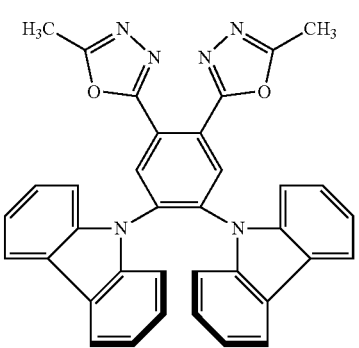

IV

-continued

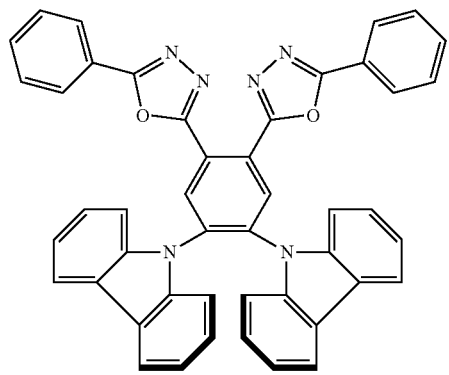

V

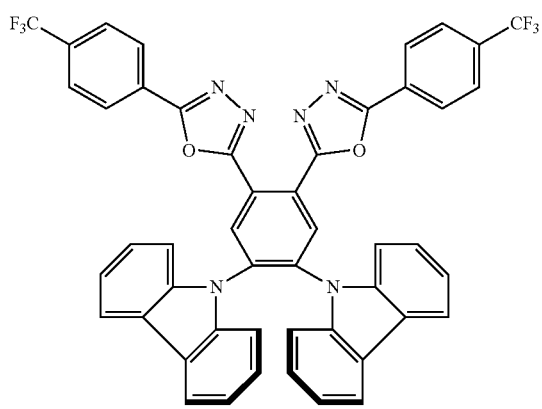

VI

In comparison with the known TADF emitter "2CzPN":

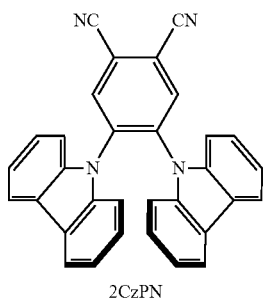

2CzPN these compounds exhibit improved TADF properties as described below, under the heading "Detailed Description of Some Embodiments and Experimental Results".

In general the weaker acceptor strength of the moieties Het compared with cyano groups provides a bluer emission, considering the intramolecular charge transfer (ICT) nature of emission in TADF emitters. Furthermore, according to DFT calculations, the LUMO density of 2CzPN is mostly located on the central benzene ring whereas that of Het moieties such as oxadiazoles may be expected to be located on the heterocyclic ring. This implies that the electron density of HOMO and LUMO in compounds of the invention should be more segregated than in 2CzPN, resulting in more efficient TADF. Indeed, all these expectations are fulfilled as supported by the blue-shifted emission and shorter emission lifetime of the delayed component of emission exhibited by IV, V and VI, when compared with the prior art 2CzPN.

The synthesis of compounds according to the first aspect of the invention can be achieved by those skilled in the art. For example, and as illustrated by examples provided hereafter, the groups Het can be formed on an existing TADF structure by reaction at a nitrile. Other means of building or attaching groups Het to an aromatic (spacer) ring are well known. Similarly methods for attaching donor moieties D to an aromatic (spacer) ring are available to the skilled person. (For example in: Name reactions in heterocyclic chemistry 2005—Jie jack Li, editor; Wiley; and Strategic Applications of Organic Named Reactions in Organic Synthesis 2005— by Laslo Kurti and Barbara Czako; Academic Press. The content of these documents are incorporated by reference herein). Conveniently the addition of donor moieties D may be by nucleophilic aromatic substitution reactions such as are employed to provide carbazole substituents on prior art TADF molecules like 2CzPN.

The use of different donor moieties D on the compounds of the invention affords the opportunity to adjust the photo physical properties of TADF structures. More generally the donor moieties described herein can provide useful alternatives to the carbazole or modified carbazole moieties typically employed in some prior art TADF structures such as 2CzPN. Thus according to a second aspect the present invention provides a compound according to formula Ic:

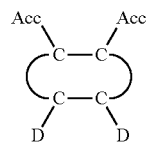

Ic wherein the ring II:

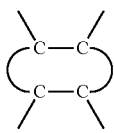

II represents an aromatic spacer ring wherein each Acc is an acceptor moiety with each acceptor moiety Acc bonded to adjacent carbon atoms, each D is a donor moiety and each donor moiety D bonded to adjacent carbon atoms, and wherein one of the donor moieties D is according to formula A and the other is according to formula A or according to formula B:

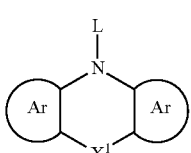

A

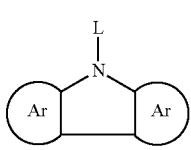

B wherein -L represents the bonding position to ring II;
$X^1$ is selected from the group consisting of O, S, NR, $SiR_2$, PR and $CR_2$, wherein each R is independently selected from the group consisting of —H, alkyl, aryl or heteroaryl (for example substituted or unsubstituted C1-C20 or even C1-C10); and

represents, independently for each occurrence a substituted or unsubstituted aryl or heteroaryl ring fused to the central ring of structures A or B, for example a five or a six membered substituted or unsubstituted aryl or heteroaryl ring.

Substituents on

where present, can include phosphine oxide or phosphine sulphide, as discussed above, to moderate the donor properties.

The ring II may be a benzene ring and thus the compound of formula Ic may be according to formula IIIc:

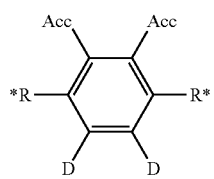

IIIc wherein D and Acc have the same meaning as before. R* may be, independently for each occurrence, selected from the group consisting of —H, alkyl, aryl or heteroaryl (for example substituted or unsubstituted C1-C20 or even C1-C10

The compounds according to formula Ic or IIIc exhibit TADF behaviour. The acceptor moieties Acc act as acceptor groups and the donor moieties D act as donor groups. The spatial separation of Acc and D by the ring II provides segregation of the HOMO (centred on donors D) and LUMO (centred on acceptors Acc) that provides efficient TADF behaviour.

The donor moieties according to formula A may moderate the photo physical behaviour of the TADF structure and can provide improved robustness to the molecules. Prior art typical TADF structures make use of only carbazole derived donor moieties D when having a similar "cruciform" structure—two acceptor groups and two donor groups as depicted in formula Ic. Moderation of the photo physical properties can include shifting of the emission spectra towards the red end of the spectrum. This effect can be related to the increased donor strength provided by donor groups D. Thus this aspect of the invention allows the production of light emitting devices based on the general structure of formula Ic with red shifted, including red, emission spectra.

The acceptor moieties Acc may be selected from the group consisting of acceptor moieties Het as described herein, —CN and other acceptors such as sulfoxide, imine, amide, sulfone, acridine, acridinium, carboxylate ester, phosphine oxide, phosphine sulfide, ketone and aldehyde. Conveniently the acceptor moieties may both be the same. Alternatively they may be different.

The moieties D of formula A in formula Ic may be selected from:

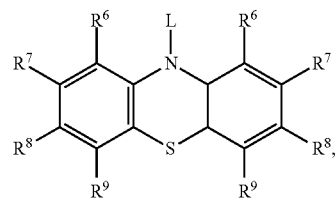

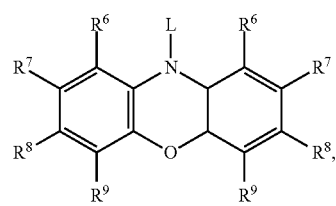

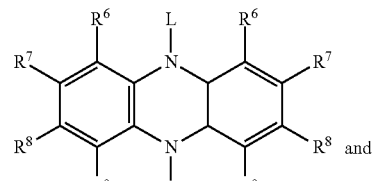

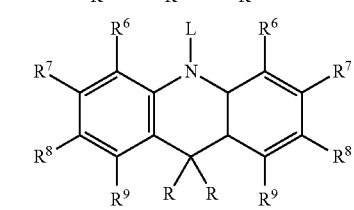

wherein the groups R, $R^6$, $R^7$, $R^8$ and $R^9$ may take the same meaning as before.

Examples of compounds according to formula Ic include compounds of formulas VIII, IX and X:

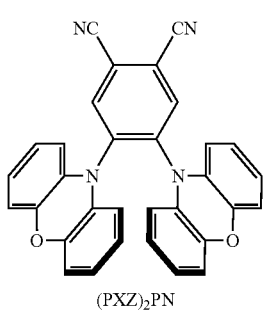

VIII $(PXZ)_2PN$

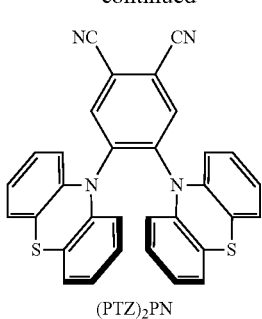

(PTZ)₂PN

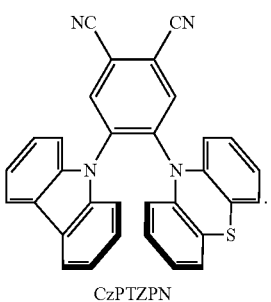

CzPTZPN

In these compounds acceptor groups Acc are —CN and donor moieties D employed are phenoxazine (VIII), phenothiazine (IX) and both phenothiazine and carbazole (X). To further modify the properties of these structures, the nitrile acceptor moieties —CN may be modified as described herein and in accordance with the first aspect of the invention to be acceptor moieties -Het.

According to a third aspect the present invention provides a charged organic species according to formula Ia:

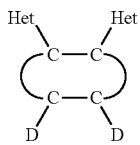

Ia wherein the ring II:

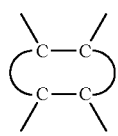

II represents an aromatic spacer ring with each Het bonded to adjacent carbon atoms and each moiety D bonded to adjacent carbon atoms;
 wherein each Het is an aromatic heterocyclic moiety and each D is a donor moiety.

Sufficient counter ions C are provided to balance the charge on the charged species of formula Ia.

The charged organic species according to formula Ia exhibits TADF behaviour. The aromatic heterocyclic groups Het act as acceptor groups and the donor moieties D act as donor groups. The spatial separation of Het and D by the ring II provides segregation of the HOMO (centred on donors D) and LUMO (centred on acceptors Het) that provides efficient TADF behaviour.

Thus organic salts of the form Ib:

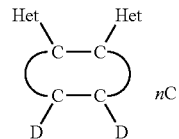

Ib where C is a counter ion with opposite charge to that provided on the ring structure including the groups Het and D, and n is at least one, can be employed in OLEDs by virtue of their TADF behaviour. In addition they may be employed in use in a LEEC, by virtue of the charge and corresponding counter ions.

The TADF species Ia can provide the benefits in terms of high efficiencies found with OLED devices but in use in a LEEC, by virtue of the charge and corresponding counter ions. (i.e. salts Ib). The charged organic thermally activated delayed fluorescence (TADF) species Ia and its accompanying counter ions can present the advantage of good solubility allowing solution processing, for example inkjet type printing when fabricating display devices, especially when fabricating large displays. Other benefits of LEECs can be realised, such as the ability to fabricate the device in air and the ability to use air stable electrodes.

The charged species of the invention may be according to formula IIIa:

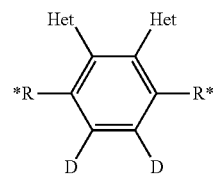

IIIa wherein D and Het have the same meaning as for formula Ia. R* may be, independently for each occurrence, selected from the group consisting of —H, alkyl, aryl or heteroaryl (for example substituted or unsubstituted C1-C20 or even C1-C10; the aromatic heterocyclic moieties Het may be, independently for each occurrence selected from the group consisting of:

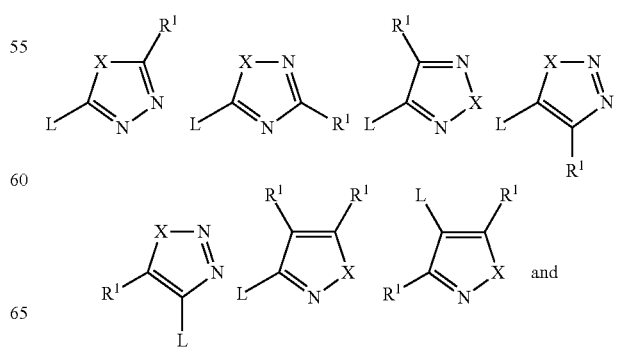

and

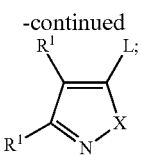

wherein -L represents the bonding position to ring II or III, X represents O, S or NR² and groups R² are, independently for each occurrence, selected from the group consisting of —H, substituted or unsubstituted primary, secondary or tertiary alkyl, that may be cyclic and may be unsaturated (for example C1-C10 or even C1-C4); substituted or unsubstituted aryl or heteroaryl;

wherein groups R¹ are, independently for each occurrence, selected from the group consisting of —H, substituted or unsubstituted primary, secondary or tertiary alkyl, that may be cyclic and may be unsaturated (for example C1-C10 or even C1-C4); substituted or unsubstituted aryl or heteroaryl, —CF₃, —OMe, —SF₅, —NO₂, halo (e.g. fluoro, chloro, bromo and iodo), aryl, aryl hydroxy, amino, alkoxy, alkylthio, carboxy, cyano, thio, formyl, ester, acyl, thioacyl, amido, sulfonamido, carbamate, phosphine oxide, phosphine sulphide and the like;

and wherein at least one of the occurrences R* and R¹ represents the bonding position, either directly or via a linking group L, to a charged group Z and/or at least one of the donor moieties D includes a charged group Z directly attached or attached via a linking group L.

Moieties D and Het in the charged species may take the form described above with respect to the first aspect of the invention.

The linking group L is optional for each occurrence of groups Z. Conveniently where linking groups L are employed, one is used for each group Z.

Where present the linking group L may, independently for each occurrence, comprise or consist of a hydrocarbylene chain, for example C1 to C30 or even C1 to C10, that may be substituted or unsubstituted, hydrocarbylene or unsaturated hydrocarbylene. The hydrocarbylene chain can include substituted or unsubstituted saturated, unsaturated or aromatic rings. For example the hydrocarbylene chain may include or consist of substituted or unsubstituted cyclopentane-1,3-diyl, cyclohexane-1,4-diyl, 1,4-phenylene or 4,4'-biphenylene moieties. Aromatic rings where present may be aryl or heteroaryl.

Where the linking group L is substituted it may be independently substituted for each occurrence. For example once, twice, or three times, e.g. once, i.e. formally replacing one or more hydrogen atoms of the hydrocarbylene chain. Examples of such substituents are halo (e.g. fluoro, chloro, bromo and iodo), —SF₅, —CF₃, —OMe, —NO₂, substituted or unsubstituted primary, secondary or tertiary alkyl, that may be cyclic and may be unsaturated (for example C1-C10 or even C1-C4); substituted or unsubstituted aryl or heteroaryl, aryl hydroxy, amino, alkoxy, alkylthio, carboxy, cyano, thio, formyl, ester, acyl, thioacyl, amido, sulfonamido, carbamate and the like. Where the substituent is amino it may be NH₂, NHR or NR₂, where the substituents R on the nitrogen may be alkyl, aryl or heteroaryl (for example substituted or unsubstituted C1-C20 or even C1-C10).

In addition to substitution options for linking groups L as discussed above, similar options for substitution may be employed for other groups or substituents that may be substituted or unsubstituted as described herein. Thus groups that may be substituted may be, for example, substituted once, twice, or three times, e.g. once, i.e. formally replacing one or more hydrogen atoms of the group. Examples of such substituents are halo (e.g. fluoro, chloro, bromo and iodo), —SF₅, —CF₃, —OMe, —NO₂, substituted or unsubstituted primary, secondary or tertiary alkyl, that may be cyclic and may be unsaturated (for example C1-C10 or even C1-C4); substituted or unsubstituted aryl or heteroaryl, aryl hydroxy, amino, alkoxy, alkylthio, carboxy, cyano, thio, formyl, ester, acyl, thioacyl, amido, sulfonamido, carbamate and the like. Where the substituent is amino it may be NH₂, NHR or NR₂, where the substituents R on the nitrogen may be alkyl, aryl or heteroaryl (for example substituted or unsubstituted C1-C20 or even C1-C10).

Where the linking group includes one or more rings they may be cycloalkyl they may be for example cyclohexyl or cyclopentyl rings. The cyclohexyl or cyclopentyl groups if present may be saturated or unsaturated and may be substituted as described above.

A linking group L may also include heteroatoms in a hydrocarbylene chain, for example by substituting one or more carbon atoms in the chain e.g. one, two, or three carbon atoms with any one of O, N, or S for example.

Examples of unsubstituted hydrocarbylene chains for group L include:

—CH₂—(CH₂)ₙ—, wherein n is from 0 to 10 or even 0 to 5 and optionally containing one or more unsaturations; cyclopentane-1,3-diyl; cyclohexane-1,4-diyl; 1,4-phenylene; 4,4'-biphenylene.

Non-metal charged groups Z may be, independently for each occurrence, positively or negatively charged. Counter ions C will have the opposite charge.

Where groups Z are positively charged they may be, independently for each occurrence, selected from the group consisting of quaternary nitrogen cations, and quaternary phosphorus cations. Conveniently all groups Z will be the same.

Where groups Z are negatively charged they may be provided with anionic substituents such as carboxylate, sulfonate, sulfinate, phosphonate, cyanide and thiocyanate.

Examples of quaternary nitrogen groups Z include:

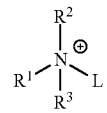

1

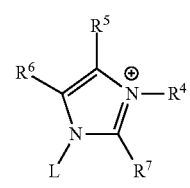

2

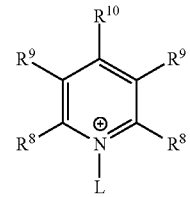

3

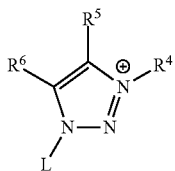

4 wherein -L indicates the position of bonding to a linking group L or directly to a charged moiety of formula Ia or IIIa; $R^1, R^2, R^3, R^4, R^5, R^6, R^7, R^8, R^9$ and $R^{10}$ are, independently for each occurrence, selected from the group consisting of —H, substituted or unsubstituted primary, secondary or tertiary alkyl, that may be cyclic and may be unsaturated (for example C1-C10 or even C1-C4); substituted or unsubstituted aryl or heteroaryl, —$CF_3$, —OMe, —$SF_5$, —$NO_2$, halo (e.g. fluoro, chloro, bromo and iodo), aryl, aryl hydroxy, amino, alkoxy, alkylthio, carboxy, cyano, thio, formyl, ester, acyl, thioacyl, amido, sulfonamido, carbamate and the like. Where the substituent is amino it may be $NH_2$, NHR or $NR_2$, where the substituents R on the nitrogen may be alkyl, aryl or heteroaryl (for example substituted or unsubstituted C1-C20 or even C1-C10).

Where the quaternary nitrogen is pyridynyl as in structure 3 the attachment to linking group L or directly to a TADF moiety may be to a carbon rather than to the nitrogen, Thus the quaternary nitrogen group Z may take the form of structure 5:

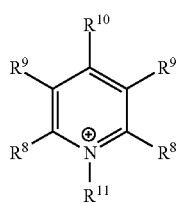

5 wherein one of $R^8$, $R^9$, $R^{10}$ and $R^{11}$ bonds to a linking group L or directly to a TADF moiety and the others of $R^8$, $R^9$, $R^{10}$ and $R^{11}$, independently for each occurrence selected from the group consisting of —H, substituted or unsubstituted primary, secondary or tertiary alkyl, that may be cyclic and may be unsaturated (for example C1-C10 or even C1-C4); substituted or unsubstituted aryl or heteroaryl, —$CF_3$, —OMe, —$SF_5$, —$NO_2$, halo (e.g. fluoro, chloro, bromo and iodo), aryl, aryl hydroxy, amino, alkoxy, alkylthio, carboxy, cyano, thio, formyl, ester, acyl, thioacyl, amido, sulfonamido, carbamate and the like. Where the substituent is amino it may be $NH_2$, NHR or $NR_2$, where the substituents R on the nitrogen may be alkyl, aryl or heteroaryl (for example substituted or unsubstituted C1-C20 or even C1-C10).

Where groups $R^1, R^2, R^3, R^4, R^5, R^6, R^7, R^8, R^9$ and $R^{10}$ are aryl, heteroaryl or cycloalkyl and are substituted, they may be substituted with substituted or unsubstituted primary, secondary or tertiary alkyl, that may be cyclic and may be unsaturated (for example C1-C10 or even C1-C4); substituted or unsubstituted aryl or heteroaryl, —$CF_3$, —OMe, —$SF_5$, —$NO_2$, halo (e.g. fluoro, chloro, bromo and iodo), aryl, aryl hydroxy, amino, alkoxy, alkylthio, carboxy, cyano, thio, formyl, ester, acyl, thioacyl, amido, sulfonamido, carbamate and the like. Where the substituent is amino it may be $NH_2$, NHR or $NR_2$, where the substituents R on the nitrogen may be alkyl, aryl or heteroaryl (for example substituted or unsubstituted C1-C20 or even C1-C10).

Thus examples of quaternary nitrogen groups Z include:

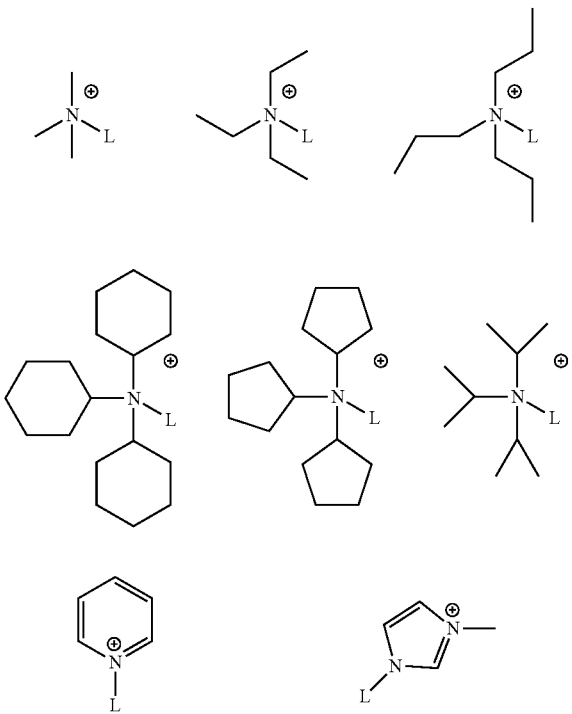

wherein -L indicates the position of bonding to a linking group L or directly to a TADF moiety.

Examples of quaternary phosphorus groups Z include:

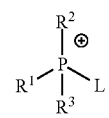

6 wherein $R^1$, $R^2$ and $R^3$ have the same meaning as for the corresponding quaternary nitrogen group 1 discussed above and wherein -L indicates the position of bonding to a linking group L or directly to a TADF moiety.

Thus examples of quaternary phosphorus groups Z include:

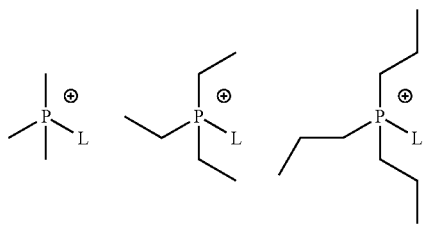

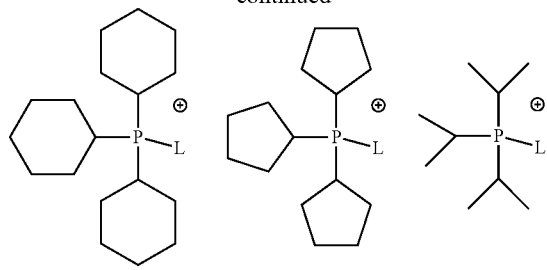

R is an aryl group, for example phenyl; $OTf^{--}$, $OTs^{--}$, $SbX_6^{--}$ wherein X is halide, $NTf_2^{--}$ $NO_3^{--}$, $CO_3^{2--}$; cations of first and second group elements in the periodic table and quaternary ammonium cations.

Exemplary structures according to the second aspect of the invention may take the same form as those discussed above with respect to the first aspect of the invention, with the addition of at least one charged group Z, each optionally attached by a linking group L.

For example, where a carbazole moiety is used as donor moiety D the charged species may take the general form VII:

VII wherein at least one of groups $R^8$ (para to the carbazole nitrogen) is of the form -L-Z wherein L is a linking group and Z a charged group as discussed herein.

Synthesis of the charged organic thermally activated delayed fluorescence (TADF) species and sufficient counter ions to balance the charge on the charged organic thermally activated delayed fluorescence (TADF) species can be carried out by a skilled person.

These salts may be made by modification of the TADF species to provide charged species and the desired counter ion or counter ions may be present in the synthetic route to the charged species or introduced by suitable ion exchange procedures.

For example, carbazole or similar donor moieties D of the TADF molecules may be modified before and/or after synthesis of the TADF molecule to provide a charged group or groups.

An exemplary synthetic route is shown below in Scheme A.

wherein -L indicates the position of bonding to a linking group L or directly to a TADF moiety.

The counter ion or counter ions C may be selected from the group consisting of: halide, $PF_6^-$, $BF_4^-$, $BR_4^{--}$; wherein Scheme A. Synthesis of charged TADF emitters.

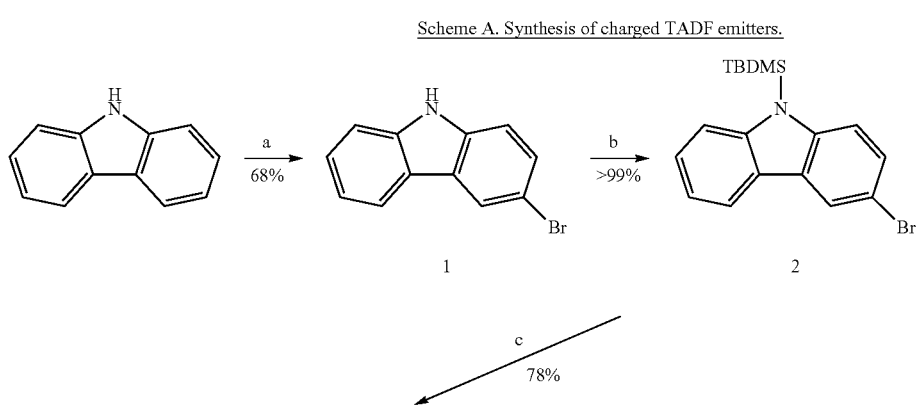

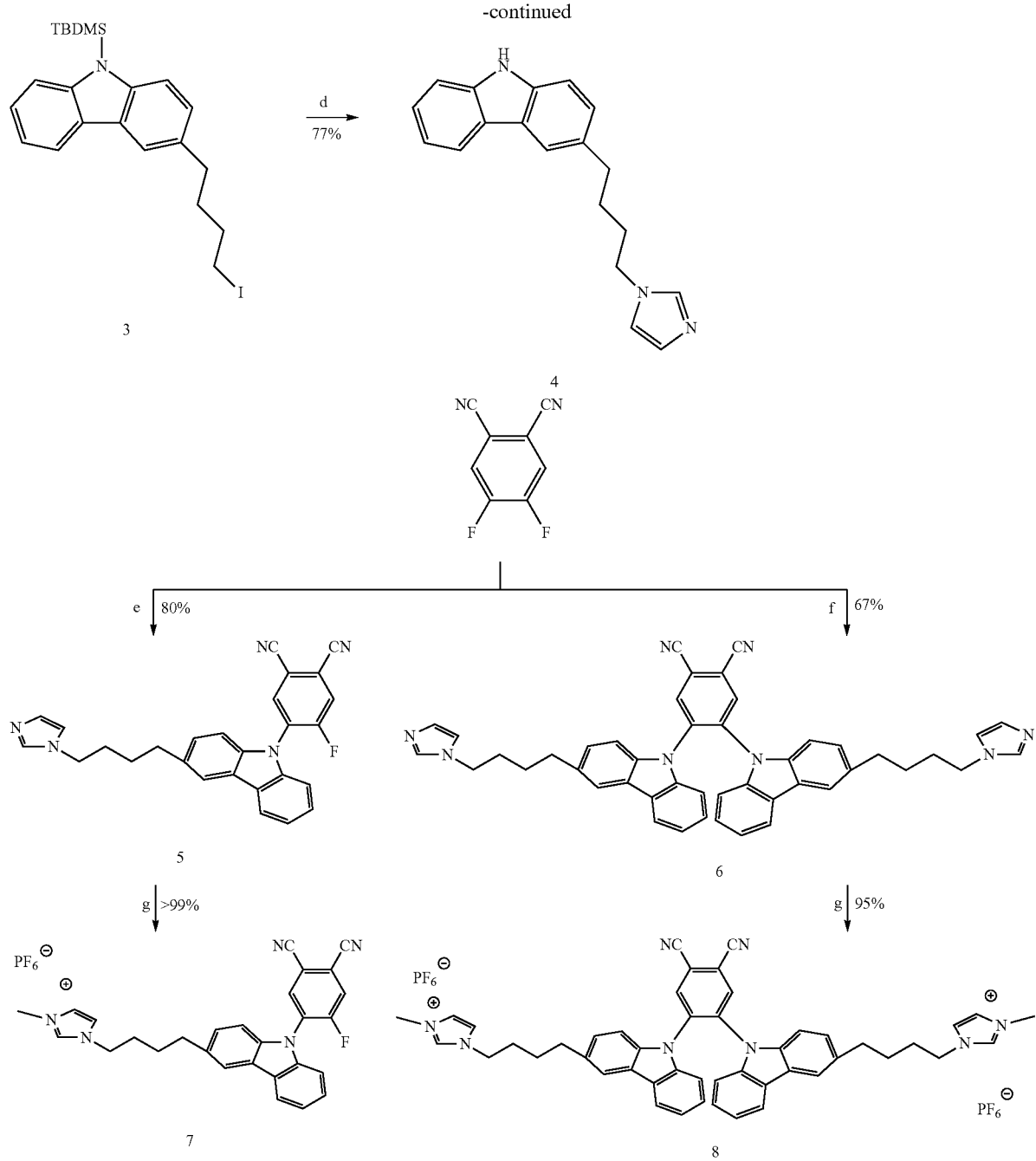

a. NBS, ACN, rt, 1 h. b. i) NaH, THF, rt, 30 min, ii) TBDMSiCl c. i) n-BuLi, THF, -78° C., 30 min, ii) excess 1,4-diiodobutane.
d. NaH, imidazole, THF, reflux, 4 h. e. i) NaH, 4, THF, rt, 30 min, ii) 2 equiv. 4,5-difluorophthalonitrile, rt, 4 h. f. i) NaH, 4, THF, rt, 30 min,
ii) 0.6 equiv. 4,5-difluorophthalonitrile, rt, 4 h. g. i) MeI, ACN, 40° C., 2 h ii) sat. NH$_4$PF$_6$ (aq).

In the examples shown in the scheme A above carbazole, used as donor moiety, is modified by bromination to provide 3-bromocarbazole 1. The TBDMS protected intermediate 2 is alkylated with an iodo-hydrocarbylene group to give intermediate 3. Alkylation with imidazole provides modified carbazole 4. As shown in the scheme, the modified carbazole 4 can be used to provide TADF species 5 or 6. Quaternisation of imidazole nitrogen with methyl iodide and then exchange of iodide anion with PF$_6$ provides 7 and 8.

This general approach can be used to provide other TADF species with charged groups, optionally connected by linking groups such as hydrocarbylene linkers. For example the other donor moieties D discussed herein may be modified by synthetic routes akin to that of scheme A to add charged groups, optionally connected by linking groups. Quaternisation at N or P provides a convenient route to charged (cationic) species. Alternatively providing anionic charged species (optionally connected by linking groups L) such as carboxylate, sulfonate, sulfinate, phosphonate, cyanide and thiocyanate can be readily done by the skilled person.

Modification of the —CN groups to produce -Het groups can be carried out before or after addition of the donor groups.

The present invention also provides an OLED or other light emitting device, such as a LEEC comprising a compound or charged organic species of the invention.

According to a fourth aspect the present invention provides a TADF compound wherein at least one donor moiety (D) is substituted by at least one substituent selected from the group consisting of phosphine oxide and phosphine sulphide. Conveniently where more than one phosphine oxide or phosphine sulphide substituent is provided they may be the same. Alternatively they may be different. Where the TADF compound has more than one donor moiety (D) then all the donor moieties D may be provided with one or more phosphine oxide or phosphine sulphide substituents.

The phosphine oxide or phosphine sulphide substituent may be selected from the group consisting of:

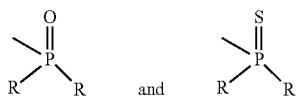

where the substituents R on the phosphorus may be alkyl, aryl or heteroaryl (for example substituted or unsubstituted C1-C20 or even C1-C10).

The phosphine oxide or phosphine sulphide substituent may have phenyl or substituted phenyl groups R on the phosphorus.

Thus substituents:

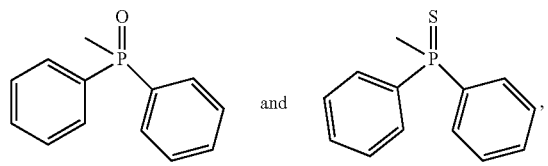

or substituents where one or both phenyl groups are substituted, are contemplated for donor moieties D.

Thus TADF compound according to the fourth aspect the present invention may be according to formula Id:

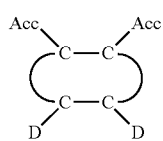

wherein the ring II:

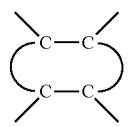

represents an aromatic spacer ring wherein each Acc is an acceptor moiety with each acceptor moiety Acc bonded to adjacent carbon atoms, each D is a donor moiety and each donor moiety D bonded to adjacent carbon atoms, and wherein the donor moieties D are independently selected from the group consisting of formula A and formula B:

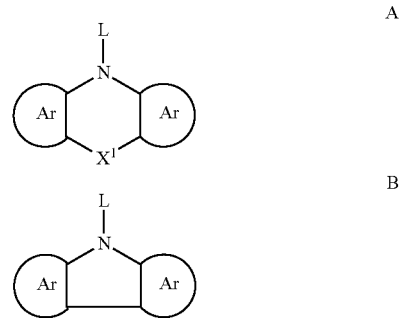

wherein -L represents the bonding position to ring II;

$X^1$ is selected from the group consisting of O, S, NR, $SiR_2$, PR and $CR_2$, wherein each R is independently selected from the group consisting of —H, alkyl, aryl or heteroaryl (for example substituted or unsubstituted C1-C20 or even C1-C10); and

represents, independently for each occurrence a substituted or unsubstituted aryl or heteroaryl ring fused to the central ring of structures A or B, for example a five or a six membered substituted or unsubstituted aryl or heteroaryl ring; and wherein
at least one substituent on at least one

present in the compound is phosphine oxide or phosphine sulphide.

DETAILED DESCRIPTION OF SOME EMBODIMENTS AND EXPERIMENTAL RESULTS

General Synthetic Procedures

Figure 1:
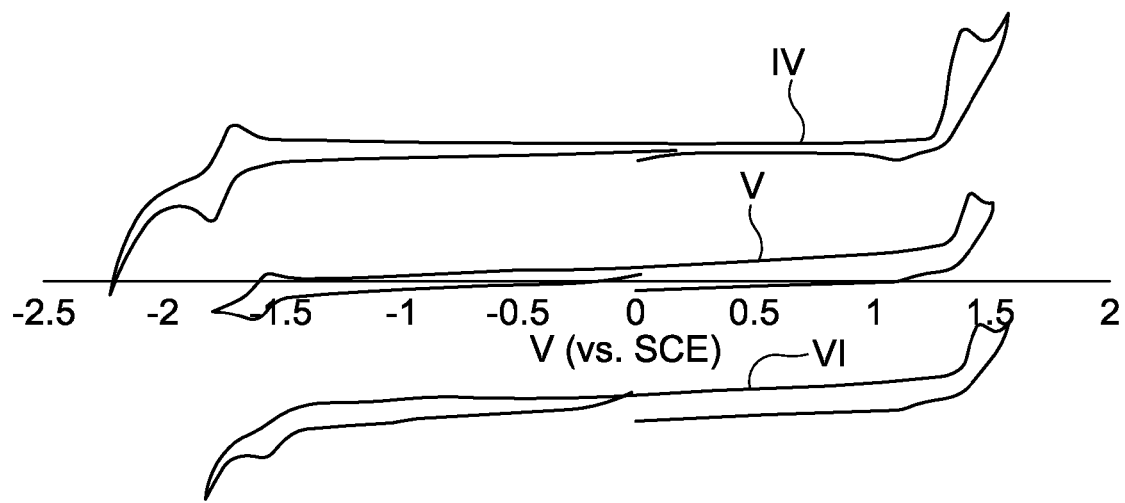
FIG. 1 shows cyclic voltammetry studies of compounds of the invention.

All the commercially available chemicals and reagent grade solvents were used as received. Air-sensitive reactions were performed under a nitrogen atmosphere using Schlenk techniques. Flash column chromatography was carried out using silica gel (Silia-P from Silicycle, 60 Å, 40-63 μm). Analytical thin-layer-chromatography (TLC) was performed with silica plates with aluminum backings (250 μm with F-254 indicator). TLC visualization was accomplished by 254/365 nm UV lamp. $^1$H, $^{13}$C and $^{19}$F NMR spectra were recorded on a Bruker Advance spectrometer. Melting points were measured using open-ended capillaries on an Electrothermal melting point apparatus and were uncorrected. High-resolution mass spectrometry (HRMS) was performed by EPSRC National Mass Spectrometry Service Centre (NMSSC), Swansea.

Synthesis of TADF Emitters with Heterocyclic Acceptor Moieties

Prior Art TADF Compound "2CzPN":

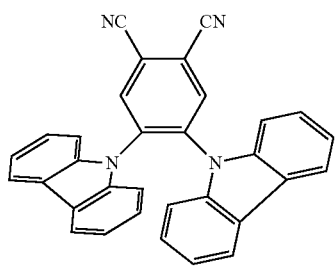 [SMILES: N#Cc1cc(-n2c3ccccc3c3ccccc32)c(-n2c3ccccc3c3ccccc32)cc1C#N]

The synthesis was largely adopted from literature. (reference 4) To a solution of carbazole (2.0 g, 12.0 mmol, 1 equiv.) in dry THF (40 mL) at room temperature was portionwise added sodium hydride (60% in mineral oil, 0.96 g, 24.0 mmol, 2 equiv.). The suspension was stirred under nitrogen protection for 15 minutes. 4,5-difluorophthalonitrile (1.2 g, 0.72 mmol, 0.6 equiv.) was added. The colour of the suspension changed from milky to red immediately and it was allowed to stir for further 3 h. Green emission (upon excitation with 365 nm UV light) slowly developed during the course of the reaction. The suspension was then slowly added to ice water and then the mixture was extracted with DCM (3×25 mL). The combined organic layers were dried with anhydrous sodium sulfate and concentrated under reduced pressure. The crude mixture was purified by flash column chromatography using DCM: Hexanes=3:2 as eluent to afford the title compound. Green solid. Yield: 74%. R$_f$: 0.39 (EtOAc: Hexanes=1:4 on silica). Mp: 332-333° C. $^1$H NMR (300 MHz, CDCl$_3$) δ (ppm): 8.33 (s, 2 H), 7.82-7.79 (m, 4 H), 7.16-7.06 (m, 12 H). $^{13}$C NMR (76 MHz, CDCl$_3$) δ (ppm): 138.4, 138.2, 135.5, 126.2, 124.3, 121.7, 120.4, 114.7, 114.5, 109.0.

The following three compounds, IV, V, VI were prepared from 2CzPN.

V

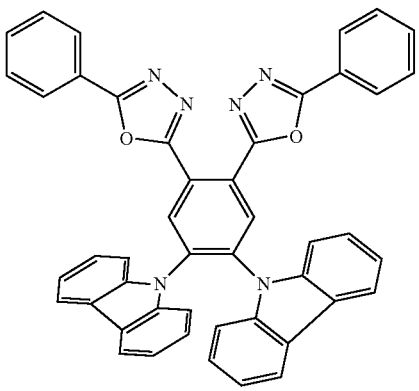

VI

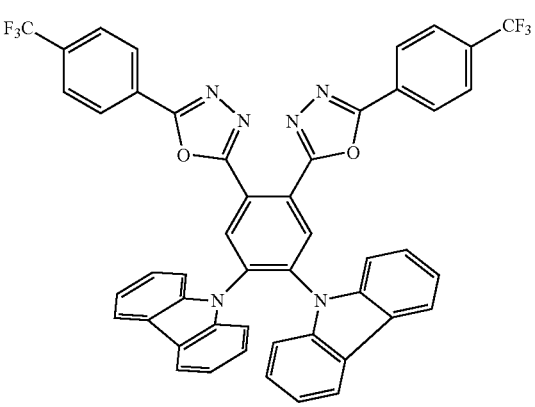

General Procedures for Synthesis of IV, V, VI.

2CzPN (120 mg, 0.26 mmol, 1.0 equiv.), ammonium chloride (84 mg, 1.56 mmol, 6.0 equiv.) and sodium azide (100 mg, 1.56 mmol, 6.0 equiv.) were mixed in DMF (2.5 mL) and heated at 110° C. for 8 h. After cooling, the reaction mixture was poured into water to afford a grey solid, which was dried and used directly without purification. The solid was then dissolved in dry pyridine (2 mL) and the appropriate acid chloride was added dropwise over 10 seconds. The reaction mixture was heated at 110° C. for 6 h. After cooling, the mixture was added to 10% HCl (10 mL). The mixture was then extracted with DCM (3×10 mL). The combined organic layer was dried with anhydrous sodium sulfate and concentrated under reduced pressure. The crude mixture was purified by flash column chromatography with ethyl acetate/hexanes as eluent.

IV:

IV

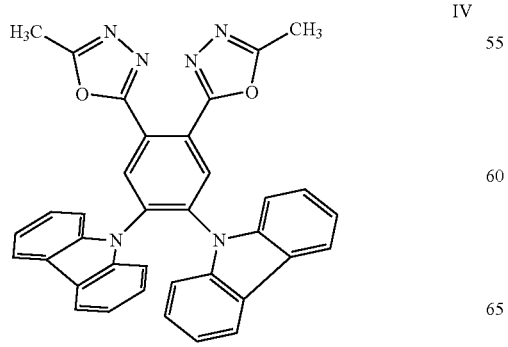

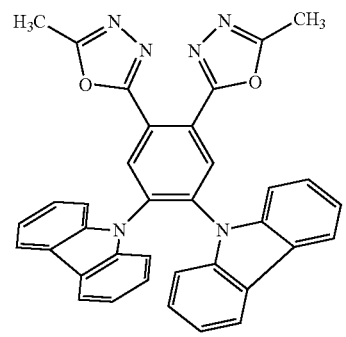 [SMILES: Cc1nnc(-c2cc(-n3c4ccccc4c4ccccc43)c(-n3c4ccccc4c4ccccc43)cc2-c2nnc(C)o2)o1]

White solid. Yield: 64%. Mp: Decompose. $R_f$: 0.25 (EA: Hexanes=3:2, silica). $^1$H NMR (300 MHz, $CD_2Cl_2$) δ (ppm): 8.47 (s, 2 H), 7.90-7.86 (m, 4 H), 7.30-7.26 (m, 4 H), 7.15-7.11 (m, 8 H), 2.61 (s, 6 H). $^{13}$C NMR (76 MHz, $CD_2Cl_2$) δ (ppm): 165.5, 163.1, 139.9, 137.5, 133.3, 126.7, 124.6, 121.5, 120.8, 110.3, 11.7. HR-MS (ESI): $[M+H]^+$ Calculated: ($C_{36}H_{25}N_6O_2$) 573.2034; Found: 573.2028.

IV:

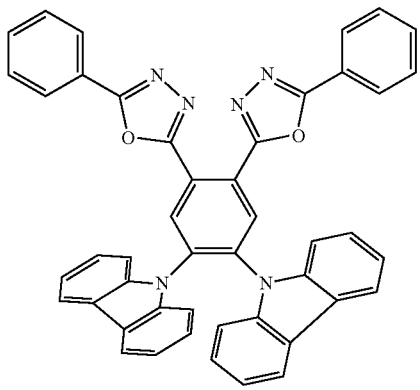 [SMILES: c1ccc(-c2nnc(-c3cc(-n4c5ccccc5c5ccccc54)c(-n4c5ccccc5c5ccccc54)cc3-c3nnc(-c4ccccc4)o3)o2)cc1]

Tan solid. Yield: 70%. Mp: 309-310° C. $R_f$: 0.25 (EA: Hexanes=1:3, silica). $^1$H NMR (400 MHz, $CD_2Cl_2$) δ (ppm): 8.68 (s, 2 H), 8.05-8.03 (m, 4 H), 7.92-7.90 (m, 4 H), 7.58-7.56 (m, 2 H), 7.52-7.48 (m, 4 H), 7.36-7.34 (m, 4 H), 7.20-7.16 (m, 8 H). $^{13}$C NMR (101 MHz, $CD_2Cl_2$) δ (ppm): 165.6, 162.2, 139.2, 137.1, 132.7, 132.1, 129.2, 126.9, 125.9, 123.9, 123.6, 123.4, 120.8, 120.1, 109.6. HR-MS: $[M+H]^+$ Calculated: ($C_{46}H_{29}N_6O_2$) 697.2347; Found: 697.2347.

VI:

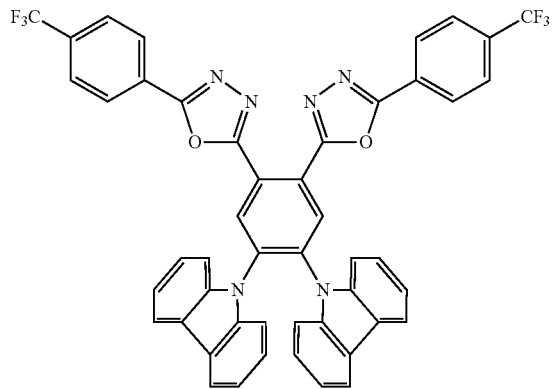 [SMILES: FC(F)(F)c1ccc(-c2nnc(-c3cc(-n4c5ccccc5c5ccccc54)c(-n4c5ccccc5c5ccccc54)cc3-c3nnc(-c4ccc(C(F)(F)F)cc4)o3)o2)cc1]

Tan solid. Yield: 71%. Mp: 179-180° C. $R_f$: 0.50 (EA: Hexanes=1:3, silica). $^1$H NMR (400 MHz, $CD_2Cl_2$) δ (ppm): 8.69 (s, 2 H), 8.20 (d, J=8.4 Hz, 4 H), 7.93-7.91 (m, 4 H), 7.79 (d, J=8.4 Hz, 4 H), 7.36-7.33 (m, 4 H), 7.19-7.17 (m, 8 H). $^{13}$C NMR (101 MHz, $CD_2Cl_2$) δ (ppm): 164.4, 162.6, 139.1, 137.3, 132.9, 127.4, 126.2, 126.2, 126.0, 123.9, 123.3, 120.9, 120.1, 109.5. $^{19}$F $\{^1H\}$ NMR (376 MHz, $CD_2Cl_2$) δ (ppm): −63.6. HR-MS (ESI) $[M+H]^+$ Calculated: ($C_{48}H_{27}F_6N_6O_2$) 833.2094; Found: 833.2104.

Photophysical Measurements.

Optically dilute solutions of concentrations on the order of $10^{-5}$ or $10^{-6}$ M were prepared in HPLC grade solvent for absorption and emission analysis. Absorption spectra were recorded at room temperature on a Shimadzu UV-1800 double beam spectrophotometer with a 1 cm quartz cuvette. Molar absorptivity values were determined from at least four solutions followed by linear regression analysis.

For emission studies, aerated solutions were bubbled by compressed air for 5 minutes and spectra were taken using the cuvette for absorption analysis. Degassed solutions were prepared via five freeze-pump-thaw cycles and spectra were taken using home-made Schlenk quartz cuvette. Steady state emission, excitation spectra and time-resolved emission spectra were recorded at 298 K using an Edinburgh Instruments F980. Samples were excited at 360 nm for steady state measurements while at 378 nm for time-resolved measurements and 450 nm was monitored for excitation spectra. Photoluminescence quantum yields for solutions were determined using the optically dilute method (Reference 5) in which four sample solutions with absorbances of ca. 0.10, 0.080, 0.060 and 0.040 at 360 nm were used. The Beer-Lambert law was assumed to remain linear at the concentrations of the solutions. For each sample, linearity between absorption and emission intensity was verified through linear regression analysis with the Pearson regression factor ($R^2$) for the linear fit of the data set surpassing 0.9. Individual relative quantum yield values were calculated for each solution and the values reported represent the slope obtained from the linear fit of these results. The equation $\Phi_s=\Phi_r(A_r/A_s)((I_s/I_r)(n_s/n_r)^2$ was used to calculate the relative quantum yield of the sample, where ($\Phi_r$) is the absolute quantum yield of the external reference quinine sulfate ($\Phi_r$=54.6% in 1 N $H_2SO_4$), (Reference 6). A stands for the absorbance at the excitation wavelength, I is the integrated area under the corrected emission curve and n is the refractive index of the solvent. The subscripts "s" and "r" representing sample and reference, respectively. The experimental uncertainty in the emission quantum yields is conservatively estimated to be 10%, though we have found that statistically we can reproduce PLOYs to 3% relative error. An Integrating sphere was employed for quantum yield measurements for thin film samples.

Electrochemistry Measurements.

Cyclic Voltammetry (CV) analysis was performed on an Electrochemical Analyzer potentiostat model 600D from CH Instruments. Samples were prepared as MeCN solutions, which were degassed by sparging with MeCN-saturated argon gas for 15 minutes prior to measurements. All measurements were performed using 0.1 M MeCN solution of tetra-n-butylammonium hexafluorophosphate. An $Ag/Ag^+$ electrode was used as the reference electrode while a platinum electrode and a platinum wire were used as the working electrode and counter electrode, respectively. The redox potentials are reported relative to a saturated calomel electrode (SCE) with a ferrocenium/ferrocene ($Fc^+$/Fc) redox couple as the internal standard (0.38 V vs SCE).

OLED Fabrication and Characterization.

A pre-patterned ITO glass substrate (FIG. 2) was treated by ultrasonic cleaning in acetone and propan-2-ol consecutively and then being treated by oxygen plasma. A PEDOT:PSS layer was spin-coated on the ITO substrate and subsequently baked at 120° C. for 10 minutes inside the glove-box to remove the residual moisture. Around 30 nm thick layer of PVK, acting as the hole-transporter, was spin-coated from a chlorobenzene solution and then baked at 120° C. for another 10 minutes. After spin-coating the emitting layer onto PVK, the sample was transferred into the vacuum chamber. A layer of electron-transporting material, B3PYMPM, was thermally deposited. Finally, Ca/Al as the composite cathode was thermally deposited through a shadow mask in the vacuum chamber under a pressure of ~2.0×10⁻⁶ mbar. All the devices were encapsulated with UV epoxy resin inside the glove-box. The luminance-current-voltage characteristics were measured in ambient environment using Keithley 2400 source meter and a 2000 multimeter connected to a calibrated Si photodiode. The external quantum efficiency was calculated with the assumption of a Lambertian distribution. The electroluminence spectrum was captured by an Andor DV420-BV CCD spectrometer.

Results and Discussion
Synthesis

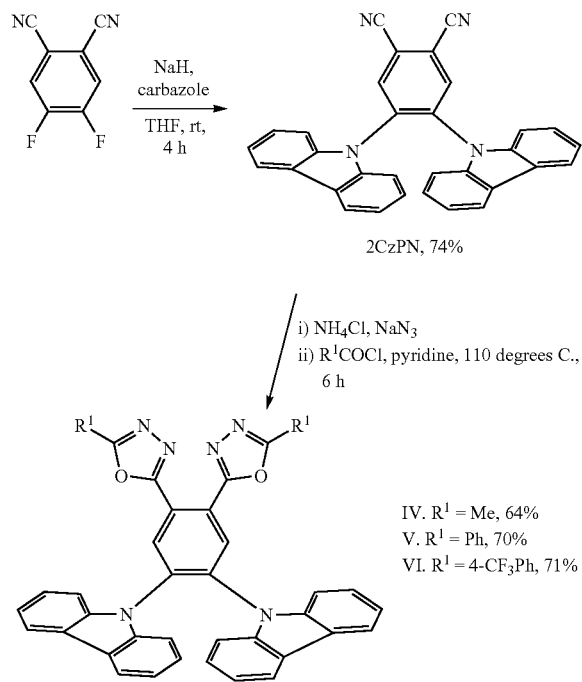

Scheme 1. Synthesis of IV, V and VI.

The synthetic route for IV, V and VI is shown in Scheme 1.

Despite the many synthetic routes available for the installation of the oxadiazole motif, (Reference 7) a two-step protocol, passing through a tetrazole intermediate is the most straightforward (Reference 4), given the presence of the cyano groups in the known 2CzPN. Thus, 2CzPN was reacted with ammonium chloride and NaN₃ in DMF at 110° C. to give the tetrazole intermediates, which were subsequently directly reacted with corresponding acid chlorides to provide the desired oxadiazole emitters in good yield (64-71%).

Absorption and Electrochemistry

TABLE 1

Summary of absorption and electrochemistry of IV, V and VI and 2CzPN as control.

| Compound | $\lambda_{abs}{}^a$ (nm), [ε (×10⁴ M⁻¹ cm⁻¹)] | Electrochemistry[b] (eV) |
|---|---|---|
| IV | 281 [2.26], 290 [2.46], 321 [1.37], 335 [1.51], 353 [1.36] | HOMO: −5.83<br>LUMO: −2.70<br>ΔE: 3.13 |
| V | 258 [5.38], 283 [4.39], 291 [4.48], 320 [2.38], 333 [2.20], 361 [2.12] | HOMO: −5.84<br>LUMO: −2.80<br>ΔE: 3.04 |
| VI | 257 [4.81], 283 [4.36], 291 [445], 319 [2.00], 332 [1.95], 367 [1.79] | HOMO: −5.84<br>LUMO: −2.86<br>ΔE: 2.98 |
| 2CzPN | | HOMO: −5.84<br>LUMO: −2.99<br>ΔE: 2.85 |

[a] in DCM at 298K.
[b] in MeCN with 0.1M [nBu₄N]PF₆ as the supporting electrolyte and Fc/Fc⁺ as the internal reference.
The HOMO and LUMO energies were calculated using the relation $E_{HOMO/LUMO} = -(E^{ox}_{pa,\,1}/E^{re}_{pc,\,1} + 4.8)$eV, where $E^{ox}_{pa}$ and $E^{red}_{pc}$ are anodic and cathodic peak potentials respectively.
ΔE = −(E_{HOMO} − E_{LUMO}).

The electrochemistry of IV, V and VI was studied by CV in degassed MeCN solutions under argon, FIG. 1. The HOMO levels of the dyes are practically identical (−5.83 to −5.84 eV) because they have the same carbazole donor. Yet, their LUMO levels are strongly influenced by the acceptor strength induced by the groups attached to the oxadiazole. The LUMO level of V is lower by 0.1 eV compared to IV as a result of increased conjugation length afforded by the phenyl group. Emitter VI has the most stabilized LUMO (−2.86 eV) due to the strong electron-withdrawing effect of the trifluoromethyl group. The oxidations of all three dyes are irreversible, which is not unexpected as carbazole radical cations are known to be electrochemically unstable and undergo dimerization. Only 3 shows an irreversible reduction, probably due to cleavage of the C—F bond following reduction. breakage of carbon-fluorine bond after being reduced.

Photophysics

Table 2 (below) shows a summary of photo physics measurements.

TABLE 2

Summary of solution and thin film photophysical properties of IV, V and VI Solution Photophysics

| | $\lambda_{em}{}^a$ (nm) | | | $\Phi_{PL}{}^b$ (%) | | | $\tau_e$ (ns) | |
|---|---|---|---|---|---|---|---|---|
| | PhMe | DCM | ACN | PhMe | DCM | ACN | PhMe | ACN |
| IV | 448 (76) | 487 (98) | 505 (113) | 24.5 (28.7) | 26.3 (35.3) | 15.5 (28.6) | 15.1, 1310 (1.1) | 25.0, 1180 (0.9) |
| V | 466 (80) | 502 (105) | 531 (125) | 27.5 (38.3) | 29.7 (29.9) | 14.5 (27.3) | 15.4, 1270 (1.0) | 22.6, 556 (1.3) |
| VI | 484 (88) | 518 (111) | 542 (136) | 25.7 (39.1) | 27.9 (31.4) | 12.4 (18.8) | 13.2, 1310 (1.7) | 17.7, 797 (1.5) |
| 2CzPN | 478 (88) | | | 7.9 (22.6) | | | 33.0, 14,946 | |

| Thin Film Photophysics[c] | | | |
|---|---|---|---|
| | $\lambda_{em}$ (nm) | $\Phi_{PL}{}^d$ (%) | $\tau_e$ (ns) |
| IV | 429 (69) | 39.6 (46.4) | 12, 1900 |
| V | 442 (73) | 54.5 (62.0) | 11, 1582 |
| VI | 464 (82) | 57.1 (74.9) | 12, 1989 |

[a] Emission maxima and full-width at half maximum (FWHM) are reported from degassed solutions. FWHM in parentheses.
[b] 0.5M quinine sulfate in H₂SO₄ (aq) was used as reference (PLQY: 54.6%).[10] Vallues quoted are in aerated solutions, which were prepared by bubbling with air for 5 minutes. Values in parentheses are for degassed solutions, which were prepared by five s freeze-pump-thaw cycles.
[c] Thin films were prepared by spin-coating doped samples in PMMA (10% w/w).
[d] Determined using an integrating sphere.

The solution-state photophysical properties of IV, V and VI were studied in toluene, DCM and MeCN. All the three TADF emitters show positive solvatochromism and broad and unstructured emission profiles, which are characteristic of ICT emitters. The broadness of emission, which is characterized by full width at half maximum (FWHM), also increases with increasing polarity of the solvent. Regardless of solvent, the emission maxima increase in the order: IV<V<VI, which is consistent with the bandgaps obtained from electrochemistry.

The photoluminescence quantum yields ($\Phi_{PL}$) range from 12-39% and do not significantly change with solvent choice. The quantum yields in degassed solutions are always higher than those in aerated solutions, which suggests that there is a contribution from the triplet excited state towards emission, a typical observation of TADF materials. The emission lifetimes ($T_e$) of IV, V, VI consist of both prompt (13.2-25.0 ns) and delayed (556-1310 ns) components, which are characteristic of TADF emission.

The weaker acceptor strength of oxadiazole compared to the cyano group causes a desired blue-shifted emission in emitters IV, V, VI compared with 2CzPN. Indeed, the LUMO levels of IV, V, VI range from −2.70 eV to −2.86 eV while the LUMO of 2CzPN was found to be −2.99 eV, and the emission is blue-shifted as a consequence. For example, IV has an emission maximum at 448 nm in toluene, blue-shifted by 30 nm compared with 2CzPN (478 nm) in the same solvent. In addition, the emission lifetimes of delayed components for 1-3 range from 0.5 to 1.3 µs, which are significantly shorter than that observed for 2CzPN (14.9 µs). The short delayed component of the emission lifetimes reveal a smaller singlet-triplet energy gap, which is a consequence of greater electronic separation between donor (HOMO) and acceptor (LUMO) units in IV, V, and VI compared with 2CzPN. The delayed component emission lifetimes of IV, V and VI are among the shortest of the organic TADF materials known.

For thin film measurements, high quality thin films were prepared by spin-coating DCM solution of 10 wt % dye in PMMA. All the emission maxima are blue-shifted by ~20 nm and the profiles slightly sharper compared with those measured in toluene solution. The thin film quantum yields (40-75%) are significantly higher than in solution as a result of the more rigid environment. In particular, V ($\lambda_{em}$: 442 nm) and VI ($\lambda_{em}$: 464 nm) exhibit remarkable quantum yields of 62% and 75% in the deep-blue region under nitrogen, making them useul blue TADF materials for OLED applications. Similar to their behaviour in solution, the quantum yields of the thin films are higher under a nitrogen atmosphere than when exposed to air, suggesting the presence of TADF in solid state. The emission lifetimes ($T_e$) of IV, V, VI in thin film consist of both prompt (11-12 ns) and delayed (1582-1989 ns) components, which are characteristic of TADF emission.

Electroluminescence Performances.

Figure 2:
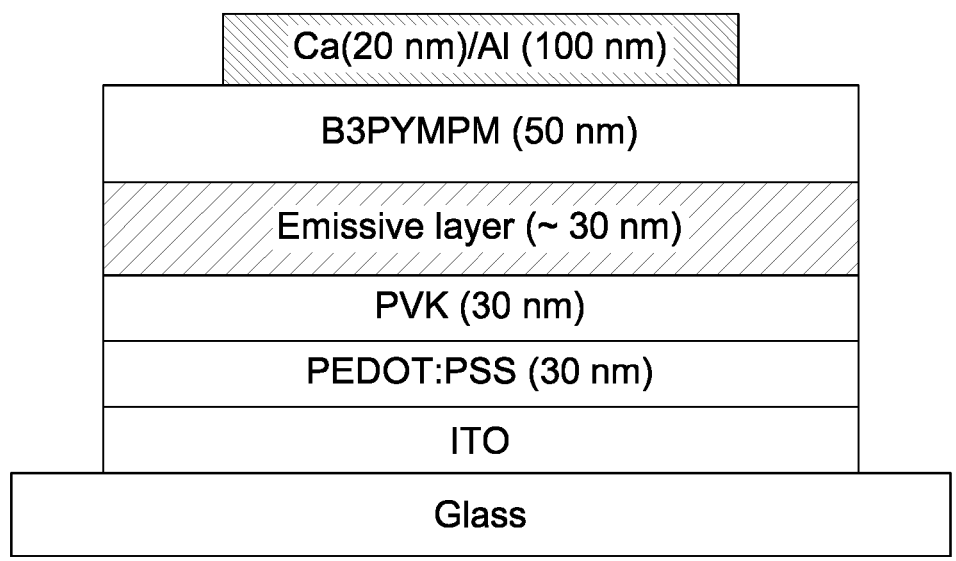
FIG. 2 shows the structure of OLEDs in schematic cross section.

A series of OLEDs based on the three emitters were fabricated with the multi-layer architecture shown in FIG. 2, where PVK, mCP and OXD-7 were used as the hole transporting layer (HTL), electron blocking layer and the exciton blocking layer (EBL), respectively while B3PYMPM was used as the electron transporting layer (ETL) layer. Ca was used to reduce the injection barrier. This multi-layer structure provides a compact emissive layer (EML) where the excitons were finely confined to enhance radiative recombination rate.

Nine devices were constructed to compare the properties of the emitters, i.e. for the emissive layer, A1: mCP:OXD-7:IV (70:20:10), A2: mCP:IV (90:10), A3: IV (without additives);

B1: mCP:OXD-7:V (70:20:10), B2: mCP:V (90:10), B3: V;

C1: mCP:OXD-7:VI (70:20:10), C2: mCP:VI (90:10), and C3: VI, respectively.

(PEDOT:PSS=poly(3,4-ethylenedioxythiophene): poly(styrenesulfonate), PVK=poly(N-vinylcarbazole), mCP=3,5′-N, N-dicarbazole-benzene, OXD-7=1,3-bis[(4-tert-butylphenyl)-1,3,4-oxadiazolyl] phenylene, B3PYMPM=bis-4,6-(3, 5-di-3-pyridylphenyl)-2-methylpyrimidine)

A summary of photo physics results for these OLEDs is given in Table 3 below.

TABLE 3

Comparison of the performance of the devices

| Device | $V_{on}^a$ (V) | $\lambda_{peak}^b$ (nm) | FWHM$^c$ (nm) | $EQE_{max}^d$ (%) | $CE_{max}^e$ (cd/A) | $PE_{max}^f$ (lm/W) | CIE$^g$ |
|---|---|---|---|---|---|---|---|
| A1 | 7.4 | 455 | 131 | 0.56 | 0.98 | 0.30 | (0.23, 0.27) |
| A2 | 7.3 | 462 | 120 | 0.73 | 1.22 | 0.41 | (0.23, 0.26) |
| A3 | 10.9 | 544 | 175 | 0.04 | 0.09 | 0.02 | (0.34, 0.42) |
| B1 | 6.0 | 466 | 106 | 1.00 | 1.84 | 0.79 | (0.21, 0.28) |
| B2 | 6.5 | 471 | 104 | 1.04 | 1.95 | 0.77 | (0.22, 0.29) |
| B3 | 9.3 | 573 | 163 | 0.24 | 0.61 | 0.17 | (0.40, 0.46) |
| C1 | 7.5 | 501 | 125 | 1.43 | 3.45 | 1.32 | (0.29, 0.40) |
| C2 | 7.1 | 497 | 123 | 2.00 | 4.81 | 2.14 | (0.27, 0.40) |
| C3 | 8.0 | 581 | 142 | 0.13 | 0.34 | 0.11 | (0.44, 0.49) |

$^a V_{on}$—Turn-on voltage @1 cd/m$^2$.
$^b \lambda_{peak}$—Peak wavelength at 1 mA/cm$^2$.
$^c$FWHM—Full width at half maximum of the EL spectrum at 1 mA/cm$^2$.
$^d EQE_{max}$—Maximum external quantum efficiency.
$^e CE_{max}$—Maximum current efficiency.
$^f PE_{max}$—Maximium power efficiency
$^g$CIE—The Commission Internationale de L'Eclairage coordinates at 1 mA/cm$^2$.

Cruciform TADF Structures Having Different Donor Moieties D

Scheme 2 (below) shows the synthetic route to TADF structures employing different nitrogen containing donor moieties D. The route is similar to that of Scheme 1 for compounds 2CzPN, VIII and IX, with minor differences.

To a solution of corresponding nitrogen donor moiety (2 equiv.) in dry THF (20 mL) was added portionwise NaH (60% in mineral oil, 4 equiv.) and the mixture was stirred for 15 mins. 4,5-difluorophthalonitrile (1 equiv.) was added and the mixture was allowed to stir for further 3 h. The mixture was slowly added to ice-water (20 mL) and extracted with DCM (20 mL×3). The combined organic phase was dried with anhydrous sodium sulfate and concentrated under reduced pressure. The residue was purified by column chromatograph using DCM:Hexanes (v/v=1:1) as the eluent. The solid obtained was further recrystallized from DCM/Hexanes (v/v=1:9) to afford the analytically pure final product.

Compound X is made in a two stage process from difluorophthalonitrile via carbazole intermediate XII CzFPN, which is itself a TADF emitter material. Also shown in Scheme 2 is the synthesis of the 3-bromocarbazole derivative XI (3-BrCz)2PN:

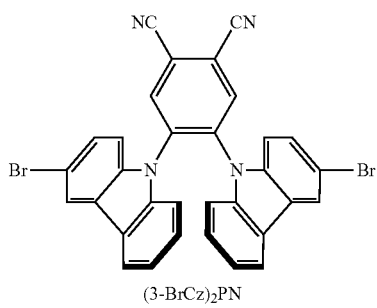

(3-BrCz)₂PN

This compound illustrates substitution on the aromatic rings of a donor moiety D.

XII was prepared in the same way as 2CzPN except that 1 equiv. of carbazole was used. Light yellow solid. Yield: 81%. $R_f$: 0.42 (EtOAc: Hexanes=1:4 on silica). Mp: 225-226° C. $^1$H NMR (300 MHz, CD$_2$Cl$_2$) δ (ppm): 8.19-8.17 (m, 3 H), 7.90 (d, J=9.2, 1 H), 7.51 (td, J=7.7, 1.2 Hz, 2 H), 7.41 (td, J=7.5, 1.0 Hz, 2 H), 7.27 (dd, J=8.2, 2.5 Hz, 2 H), $^{13}$C NMR (76 MHz, CD$_2$Cl$_2$) δ (ppm): 162.0, 158.4, 140.3, 135.4, 135.4, 131.9, 131.7, 127.5, 125.1, 124.4, 124.1, 122.6, 121.4, 116.7, 116.5, 115.0, 114.4, 114.4, 110.5, 110.4. $^{19}$F NMR (282 MHz, CD$_2$Cl$_2$) δ (ppm): 105.0. Anal. Calcd. for $C_{20}H_{10}FN_3$: C, 77.16%; H, 3.24%; N, 13.50%. Found: C, 77.14%; H, 3.16%; N, 13.41%. HR-MS (ESI) [M+NH$_4$]$^+$ Calculated: ($C_{20}H_{14}FN_4$) 329.1197; Found: 329.1200.

Scheme 2: synthesis of VIII, IX, X, intermediate XII and 3-bromocarbazole variant XI

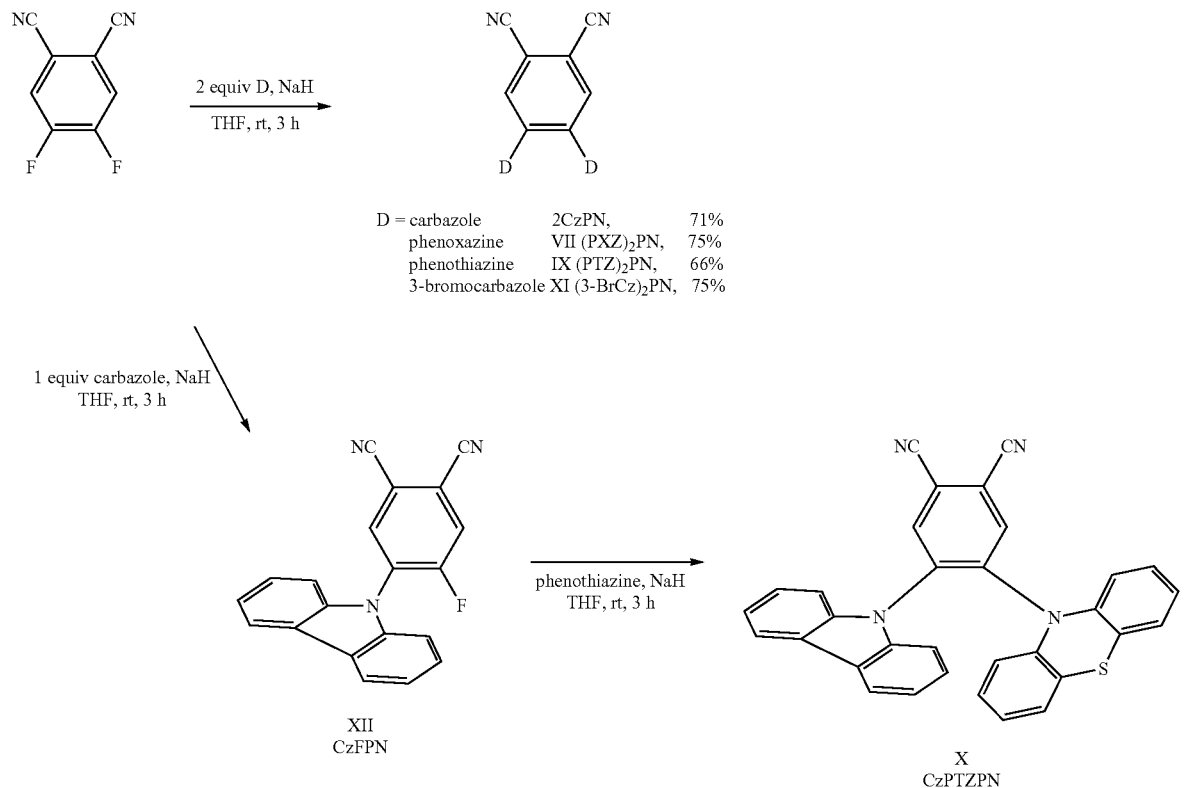

CzFPN, XII:

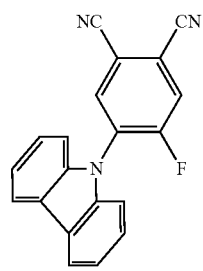 [SMILES: N#Cc1cc(F)c(-n2c3ccccc3c3ccccc32)cc1C#N]

(3-BrCz)₂PN, XI:

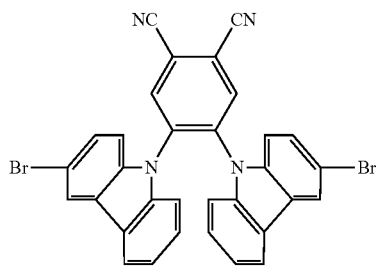 [SMILES: N#Cc1cc(-n2c3ccccc3c3cc(Br)ccc32)c(-n2c3ccccc3c3cc(Br)ccc32)cc1C#N]

Light Green solid. Yield: 75%. $R_f$: 0.39 (EtOAc: Hexanes=1:4 on silica). Mp: 315-316° C. $^1$H NMR (300 MHz, CD$_2$Cl$_2$) δ (ppm): 8.35 (s, 1 H), 8.35 (s, 1 H), 7.94 (dd, J=6.5, 1.7 Hz, 2 H), 7.87-7.82 (m, 2 H), 7.27-7.10 (m, 8 H), 6.99 (d, J=8.7, 1 H), 6.91 (d, J=8.7, 1 H). $^{13}$C NMR (76 MHz, CD$_2$Cl$_2$) δ (ppm): 139.5, 139.5, 138.6, 137.8, 137.7, 136.3, 129.6, 129.4, 128.0, 127.8, 126.8, 126.7, 124.1, 124.0, 123.9, 123.8, 122.9, 122.8, 121.5, 121.4, 116.2, 115.2, 115.2, 115.1, 111.4, 111.3, 111.1, 109.9. Anal. Calcd. for C$_{32}$H$_{16}$N$_4$Br$_2$: C, 62.36%; H, 2.62%; N, 9.09%. Found: C, 62.26%; H, 2.52%; N, 8.95%. HR-MS (ESI) [M+NH$_4$]$^+$ Calculated: (C$_{32}$H$_{20}$N$_5$Br$_2$) 634.0062; Found: 634.0059.

(PXZ)$_2$PN VIII:

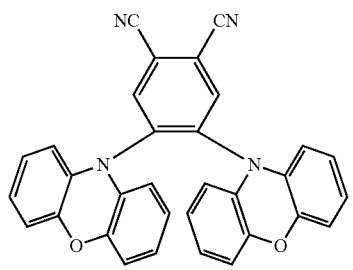 [SMILES: N#Cc1cc(N2c3ccccc3Oc3ccccc32)c(N2c3ccccc3Oc3ccccc32)cc1C#N]

Crimson solid. Yield: 58%. $R_f$: 0.46 (EtOAc: Hexanes=1:4 on silica). Mp: 375-376° C. $^1$H NMR (300 MHz, CD$_2$Cl$_2$) δ (ppm): 8.18 (s, 2 H), 6.65 (td, J=7.2, 1.4 Hz, 4 H), 6.57 (dd, J=8.0, 1.7 Hz, 4 H), 6.40 (td, J=8.0, 1.7 Hz, 4 H), 6.06 (dd, J=8.0, 1.4 Hz, 4 H), $^{13}$C NMR (76 MHz, CD$_2$Cl$_2$) δ (ppm): 145.7, 143.8, 140.9, 131.3, 124.2, 123.5, 116.9, 116.3, 115.3, 114.8. Anal. Calcd. for C$_{32}$H$_{18}$N$_4$O$_2$: C, 78.36; H, 3.70; N, 11.42. Found N/A. HR-MS (ESI) [M+Na]$^+$ Calculated: (C$_{32}$H$_{18}$N$_4$O$_2$Na) 513.1322; Found: 513.1314.

(PTZ)$_2$PN, IX:

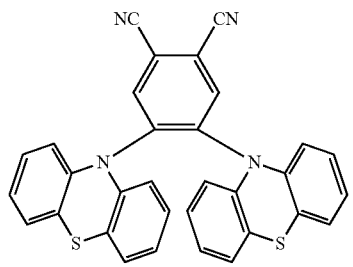 [SMILES: N#Cc1cc(N2c3ccccc3Sc3ccccc32)c(N2c3ccccc3Sc3ccccc32)cc1C#N]

Red solid. Yield: 66%. $R_f$: 0.43 (EtOAc: Hexanes=1:4 on silica). Mp: 339-340° C. $^1$H NMR (400 MHz, CDCl$_3$) δ (ppm): 7.80 (s, 2 H), 7.26-6.92 (m, 4 H), 6.81-6.79 (m, 12 H), 6.32-6.30 (m, 4 H). $^{13}$C NMR (100 MHz, CDCl$_3$) δ (ppm): 143.9, 140.7, 137.1, 127.3, 126.9, 125.3, 124.3, 118.8, 114.6, 114.1. Anal. Calcd. for C$_{32}$H$_{18}$N$_4$S$_2$: C, 73.54%; H, 3.47%; N, 10.72%. Found: C, 73.39%; H, 3.45%; N, 10.63%. HR-MS (ESI) [M+H]$^+$ Calculated: (C$_{32}$H$_{19}$N$_4$S$_2$) 523.1046; Found: 523.1032.

CzPTZPN, X:

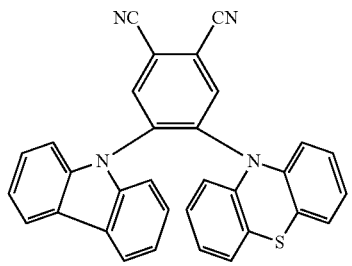 [SMILES: N#Cc1cc(N2c3ccccc3Sc3ccccc32)c(-n2c3ccccc3c3ccccc32)cc1C#N]

To a solution of phenothiazine (31.8 mg, 0.16 mmol, 1 equiv.) in dry THF (5 mL) was added portionwise NaH (60% in mineral oil, 25.6 mg, 0.32 mmol, 2 equiv.). The mixture was stirred for 15 mins. Compound 2 (50 mg, 0.16 mmol, 1 equiv.) was added and the mixture was allowed to stir for further 3 h. The mixture was slowly added to ice-water (10 mL) and extracted with DCM (10 mL×3). The combined organic phase was dried by anhydrous sodium sulfate and concentrated under reduced pressure. The residue was purified by column chromatograph using DCM:Hexanes (v/v=1:1) as the eluent. The solid obtained was further recrystallized from DCM/Hexanes mixture to afford the final product. Tan solid. Yield: 64%. $R_f$: 0.46 (EtOAc: Hexanes=1:4 on silica). Mp: 316-317° C. $^1$H NMR (300 MHz, CD$_2$Cl$_2$) δ (ppm): 8.27 (s, 1 H), 8.12 (s, 1 H), 8.00-7.97 (m, 2 H), 7.20 (td, J=7.2, 1.1 Hz, 1 H), 7.13-7.07 (m, 2 H), 6.89-6.82 (m, 3 H), 6.80-6.75 (m, 5 H), 6.57 (t, J=0.8 Hz, 1 H), 6.55 (q, J=0.5 Hz, 1 H). $^{13}$C NMR (76 MHz, CD$_2$Cl$_2$) δ (ppm): 145.5, 141.3, 140.1, 140.0, 137.8, 137.5, 127.1, 126.8, 125.7, 125.5, 124.3, 124.0, 120.8, 120.1, 117.6, 116.0, 114.8, 114.7, 114.5, 109.5. Anal. Calcd. for C$_{32}$H$_{18}$N$_4$S: C, 78.35%; H, 3.70%; N, 11.42%. Found: C, 78.37%; H, 3.71%; N, 11.41%. HR-MS (ESI) [M+NH$_4$]$^+$ Calculated: (C$_{32}$H$_{22}$N$_5$S) 508.1590; Found: 508.1572.

Absorption and Electrochemistry

Table 4 lists in Summary the absorption and electrochemistry data for compounds VIII, IX, X, XI, XII and 2CzPN.

TABLE 4

| Compound | $\lambda_{abs}{}^a$ (nm), [ε (×10$^4$ M$^{-1}$ cm$^{-1}$)] | HOMO$^b$ (eV) | LUMO$^b$ (eV) | ΔE$^b$ (eV) |
|---|---|---|---|---|
| 2CzPN | 280(sh) [1.72], 289 [2.14], 319 [1.02], 329 [1.17], 364 [1.14] | −5.88 | −2.97 | 2.91 |
| XII | 277(sh) [1.07], 286 [1.28], 316 [0.49], 331 [0.68], 348 [0.72] | −5.95 | −2.89 | 3.06 |
| XI | 261 (sh) [2.56], 285 (sh) [1.73], 294 [2.20], 326 [1.15], 340 [1.23], 362 [1.24] | −6.00 | −3.01 | 2.99 |
| VIII | 309 [0.87], 373(sh) [0.18], 443 [0.30] | −5.27 | −2.99 | 2.28 |
| IX | 297 [0.64], 313 [0.63], 424 [0.15] | −5.15 | −2.98 | 2.17 |
| X | 283 [1.55], 318 [0.84], 330 [0.77], 372 [0.52] | −5.29 | −3.01 | 2.28 |

$^a$in MeCN at 298K.
$^b$in MeCN with 0.1M [nBu$_4$N]PF$_6$ as the supporting electrolyte and Fc/Fc$^+$ as the internal reference.
The HOMO and LUMO energies were calculated using the relation $E_{HOMO/LUMO}$ = $-(E^{ox}_{pa,1}/E^{red}_{pc,1} + 4.8)$eV, where $E^{ox}_{pa}$ and $E^{red}_{pc}$ are anodic and cathodic peak potentials, respectively.
ΔE = −(E$_{HOMO}$ − E$_{LUMO}$).

Photophysics

Table 5 (below) shows a summary of photo physics measurements.

Summary of solution and thin film photophysical data of compounds VIII, IX, X, XI, XII and 2CzPN.

TABLE 5

| Emitter | In Toluene | | | Doped Film[c] | | |
|---|---|---|---|---|---|---|
| | $\lambda_{em}$[a] (nm) | $\Phi_{PL}$[b] (%) | $T_e$ (ns) | $\lambda_{em}$[a] (nm) | $\Phi_{PL}$[d] (%) | $T_e$ (ns) |
| 2CzPN | 478 | 22.6 (7.9) | 33.0, 14900 | 492 | 76.0 (62.6) | 18.4, 19700 |
| XII | 451 | 25.3 (8.5) | 13.0, 501 | 460 | 61.4 (57.7) | 11.0, 22000 |
| XI | 470 | 2.9 (2.2) | 3.5, 12100 | 478 | 52.0 (34.0) | 2.3, 22200 |
| VIII | 650 | 3.6 (1.1) | 5.0, 445 | 616 | 5.9 (5.6) | 6.6, 670 |
| IX | 674 | 1.8 (0.3) | 13.1, 776 | 622 | 3.9 (3.6) | 8.6, 540 |
| X | 656 | 2.2 (1.3) | 3.9, 279 | 600 | 5.8 (5.6) | 9.5, 1000 |

[a]Emission maxima are reported from degassed solutions.
[b]0.5M quinine sulfate in $H_2SO_4$ (aq) was used as reference (PLQY: 54.6%).[12] Values quoted are in degassed solutions. Values in parentheses are for aerated solutions.
[c]Thin films were prepared by spin-coating doped samples in PMMA (10% w/w).
[d]Values determined using an integrating sphere. Degassing was done by $N_2$ purge.

In the normalised emission spectra (see FIG. 3) compounds possessing only carbazole as the donor (compounds XI, XII and 2CzPN.) are strongly emissive in the blue to sky-blue region of the visible spectrum. Compounds possessing the much stronger PTZ (phenothiazine) and PXZ (phenoxazine) donors (VIII, IX, X) are red emissive. Compound XII shows the bluest emission of the family with an emission that is blue-shifted by 27 nm compared with the reference 2CzPN. The addition of the electron-withdrawing bromine onto the carbazole in XI likewise induces a small blue-shift of 8 nm in the emission. By contrast, phenothiazine was found to act as the strongest donor with an emission maximum in IX of 674 nm and phenoxazine promoted a smaller red-shift with an emission maximum found at 650 nm in VIII. Interestingly, the emission profile for X is blue-shifted by 18 nm compared to VIII, pointing to a HOMO in X localized on the PTZ ring but whose energy is modulated by the carbazole, most likely via π-stacking interactions.

The decay profiles of all the compounds show prompt and delayed components in degassed toluene and doped thin films, indicating TADF materials. The lifetimes of 2CzPN and XI are similar because of their similar structures. For compounds VIII, IX and X, the delayed components are much shorter (279-1000 ns) compared with 2CzPN.

OLED Devices

OLED devices for compounds VIII, IX, X, XI, XII and 2CzPN were fabricated with the same device architecture as shown in FIG. 2 with the emissive layer comprising mCP:OXD-7:Emitter material (70:20:10, 20 nm thickness).

Results summarising the Electroluminescence (EL) spectra are shown in Table 6. The breadth of emission spectrum is suggested by the FWHM values (full-width at half-maximum)

TABLE 6

Comparison of the performance of the six devices.

| Compound | $V_{on}(V)$[a] @1 cd/m² | $\lambda_{max}$ (nm)[b] | FWHM (nm) | $EQE_{max}$ (%)[c] | CIE[d] |
|---|---|---|---|---|---|
| 2CzPN | 4.8 | 508 | 109 | 4.64 | (0.26, 0.46) |
| XII | 6.1 | 526 | 152 | 0.96 | (0.30, 0.42) |
| XI | 5.5 | 507 | 123 | 3.67 | (0.29, 0.46) |
| VIII | 7.0 | 618 | 117 | 1.47 | (0.56, 0.42) |
| IX | 7.6 | 629 | 122 | 0.65 | (0.60, 0.39) |
| X | 6.2 | 617 | 119 | 1.90 | (0.58, 0.42) |

[a] Turn-on voltage.
[b]Peak emission at 1 mA/cm².
[c] Maximum external quantum efficiency.
[d]CIE at 1 mA/cm².

For the emitters with the donor units changing from carbazole to phenoxazine (VIII) or phenothiazine (IX and X), the emission color significantly shifts from bluish-green to deep-red, e.g., peak wavelength of 629 nm and CIE coordinates of (0.60, 0.39) for the emitter VIII. Tests at different current densities show that the compounds with phenoxazine and phenothiazine donors, as well as brominated carbazole donors, show extremely stable EL spectra, which are independent of the current density applied. This is in contrast with carbazole containing compounds where peak wavelength was found to shift depending on current density applied.

Synthesis of TADF Compounds Having Donor Moieties Modified with Phosphine Oxide or Phosphine Sulphide Substituents The general synthetic route is shown in Scheme 2 below. The method is illustrated by preparing TADF compounds having carbazole derived donor moieties D with cyano acceptor moieties A.

Scheme 2
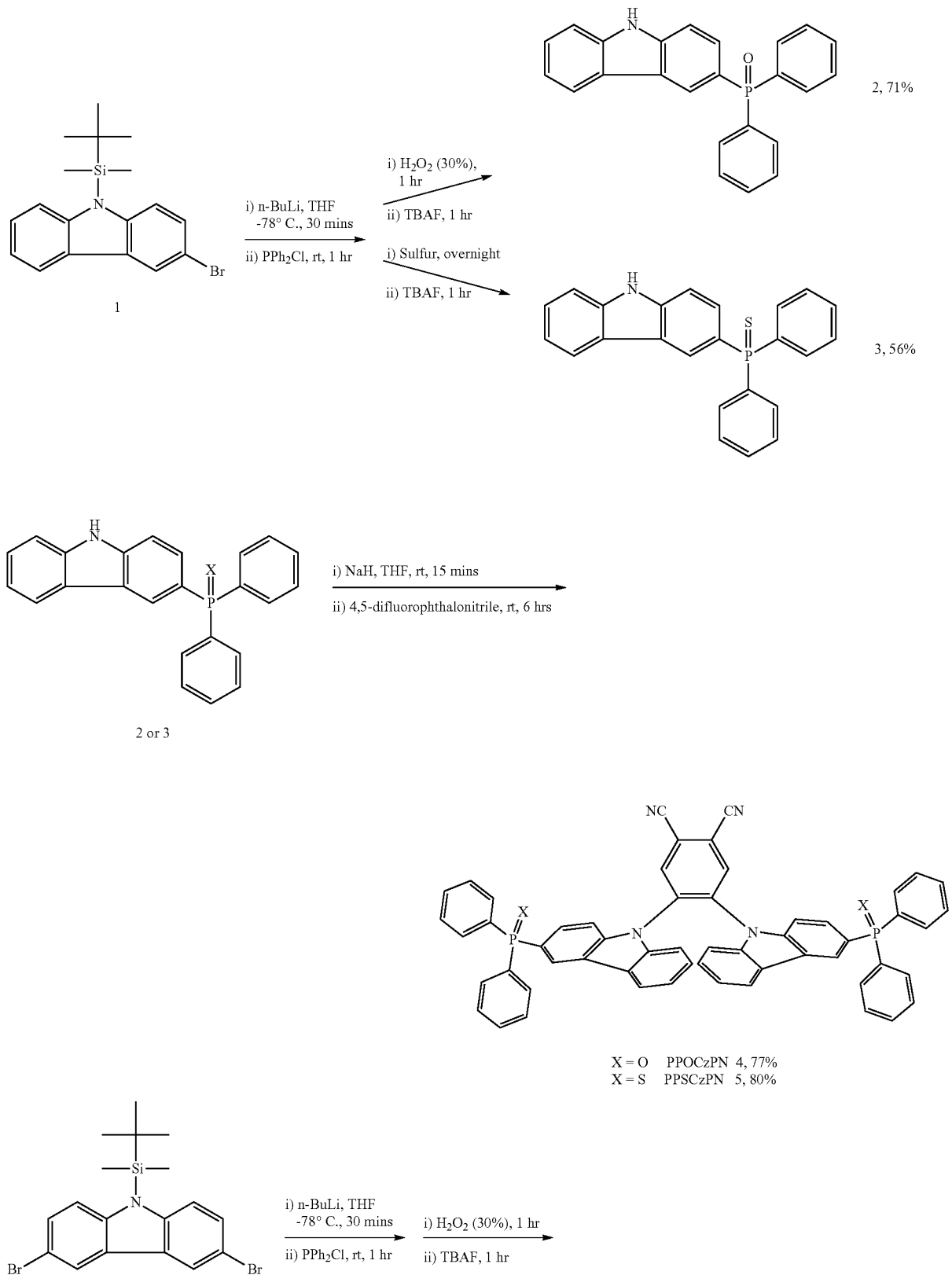

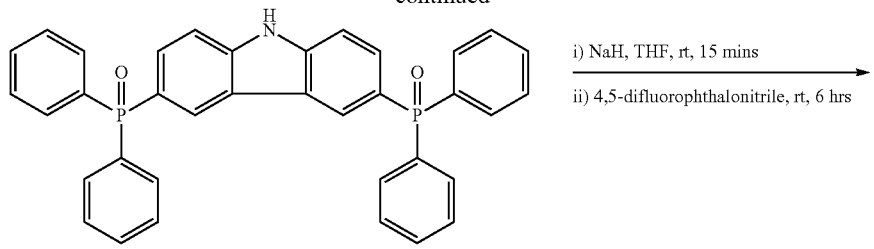

7, 48%

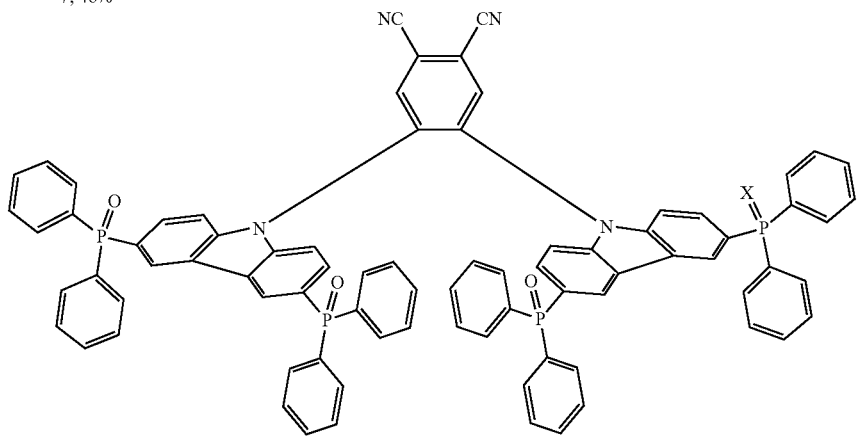

8, DiPPOCzPN

Experimental Details for Compounds 1 to 8 in Scheme 2.
Preparation of N-tert-butyldimethylsilyl-3-bromocarbazole, 1:

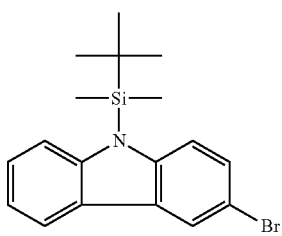 [SMILES: CC(C)(C)[Si](C)(C)n1c2ccccc2c2cc(Br)ccc21]

This was prepared by the known method (Chem. Mater., 2015, 27, 6535-6542).

Preparation of 3-(diphenylphosphoryl)carbazole, 2:

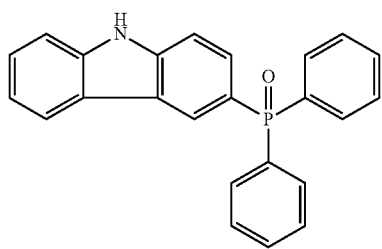 [SMILES: O=P(c1ccccc1)(c1ccccc1)c1ccc2[nH]c3ccccc3c2c1]

To a solution of 1 (500 mg, 1.4 mmol, 1.0 equiv.) in dry THF (10 mL) cooled at −78° C. was added dropwise 1.6 M n-BuLi solution (1.1 mL, 1.7 mmol, 1.2 equiv.). The reaction mixture was stirred at this temperature for 15 min. Chlorodiphenylphosphine (0.30 mL, 1.7 mmol, 1.2 equiv.) was added and the mixture was raised to room temperature, followed by stirring for 1 h. 30% $H_2O_2$ (0.6 mL, 5.1 mmol, 3.0 equiv.) was added and the mixture was stirred for 30 min. Finally, n-tetrabutylammonium fluoride (1.34 g, 5.1 mmol, 3.0 equiv.) was added and the mixture was allowed to stir for further 30 min. The mixture was added to water (10 mL) and extracted by DCM (3×10 mL). The combined organic layer was dried with anhydrous sodium sulphate. The concentrated organic layer was purified by column chromatography using EA/Hexanes (v/v 2:1) as the eluent. White solid. Yield: 71%. Mp: 310° C. $R_f$: 0.34 (EA, silica). $^1$H NMR (300 MHz, DMSO-d6) δ (ppm): 11.73 (s, 1 H), 8.49 (d, J=14.1 Hz, 1 H), 8.10 (d, J=7.8 Hz, 1 H), 7.73-7.50 (m, 13 H), 7.43 (td, J=7.7, 1.1 Hz, 1 H), 7.18 (td, J=7.5, 0.9 Hz, 1 H), $^{13}$C NMR (76 MHz, DMSO-d6) δ (ppm): 141.9, 141.9, 140.7, 134.6, 133.5, 132.3, 132.1, 132.1, 132.0, 129.3, 129.1, 129.1, 127.0, 125.2, 125.1, 122.9, 122.7, 122.3, 121.3, 121.0, 120.1, 120.0, 111.9, 111.7, 111.6. $^{31}$P NMR (121 MHz, DMSO-d6) δ (ppm): 43.24. HR-MS (ESI): [M+H]$^+$ Calculated: ($C_{24}H_{19}NOP$) 368.1199; Found: 368.1208.

Preparation of 3-(diphenylphosphorothioyl)carbazole, 3:

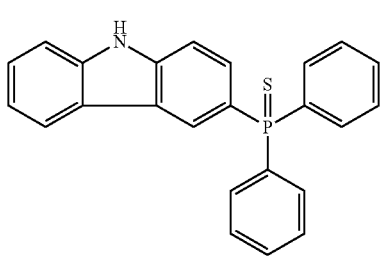 [SMILES: S=P(c1ccccc1)(c1ccccc1)c1ccc2[nH]c3ccccc3c2c1]

The title compound was prepared in the same way as 2 except elemental sulphur was added as the thionylation agent instead of 30% H$_2$O$_2$. White solid. Yield: 56%. R$_f$: 0.20 (EA: hexanes=1:3, silica). $^1$H NMR (500 MHz, CDCl$_3$) δ (ppm): 8.53 (dd, J=14.0, 1.2 Hz, 1 H), 8.35 (br, 1 H), 8.04 (d, J=7.9 Hz, 1 H), 7.82-7.71 (m, 5 H), 7.56-7.46 (m, 9 H), 7.29-7.26 (m, 1 H). $^{13}$C NMR (125 MHz, CDCl$_3$) δ (ppm): 141.2, 141.2, 139.8, 134.2, 133.5, 132.4, 132.3, 131.4, 131.4, 129.6, 129.5, 128.5, 128.4, 126.8, 125.6, 125.5, 123.5, 123.4, 122.8, 122.4, 121.7, 120.8, 120.4, 110.9, 110.7, 110.6. $^{31}$P NMR (202 MHz, CDCl$_3$) δ (ppm): 44.35.
Preparation of PPOCzPN, 4:

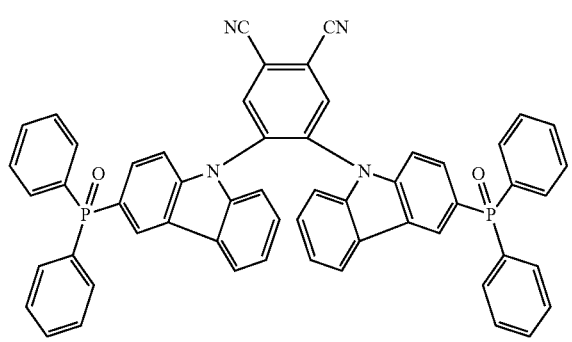 [SMILES: N#Cc1cc(-n2c3ccccc3c3cc([P@TB20](=O)(c4ccccc4)c4ccccc4)ccc32)c(-n2c3ccccc3c3cc([P@TB20](=O)(c4ccccc4)c4ccccc4)ccc32)cc1C#N]

To a solution of 2 (100 mg, 0.27 mmol, 2 equiv.) in dry THF (5 mL) was added portionwise NaH (60% in mineral oil, 21.6 mg, 0.54 mmol, 4 equiv.) and the mixture was stirred for 15 min. 4,5-difluorophthalonitrile (22.1 mg, 0.14 mmol, 1 equiv.) was added and the mixture was allowed to stir for further 3 h. The mixture was slowly added to ice-water (10 mL) and extracted with DCM (10 mL×3). The combined organic phase was dried with anhydrous sodium sulfate and concentrated under reduced pressure. The residue was purified by column chromatograph using EA:Hexanes (v/v=1:1) as the eluent. The solid obtained was further recrystallized from DCM/Hexanes (v/v=1:9) to afford the analytically pure final product. Light yellow solid. Yield: 77%. R$_f$: 0.17 (EA, silica). $^1$H NMR (300 MHz, CDCl$_3$) δ (ppm): 8.39 (s, 2 H), 8.21-8.12 (m, 2 H), 7.78-7.48 (m, 22 H), 7.23-6.90 (m, 9 H), 6.73-6.70 (m, 1 H). $^{31}$P NMR (121 MHz, CDCl$_3$) δ (ppm): 30.49, 30.39. HR-MS (ESI): [M+H]$^+$ Calculated: (C$_{56}$H$_{37}$N$_4$O$_2$P$_2$) 859.2386; Found: 859.2372.
Preparation of PPSCzPN, 5:

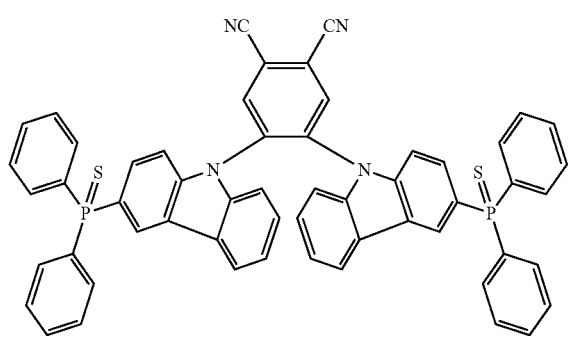 [SMILES: N#Cc1cc(-n2c3ccccc3c3cc([P@TB20](=S)(c4ccccc4)c4ccccc4)ccc32)c(-n2c3ccccc3c3cc([P@TB20](=S)(c4ccccc4)c4ccccc4)ccc32)cc1C#N]

The title compound was prepared from 3 in the same way of 4. Light yellow solid. Yield: 80%. R$_f$: 0.14 (EA: hexanes=1:3, silica). $^1$H NMR (300 MHz, CDCl$_3$) δ (ppm): 8.38 (s, 1 H), 8.37 (s, 1 H), 8.32-8.23 (m, 2 H), 7.80-7.44 (m, 24 H), 7.23-6.93 (m, 7 H), 6.66 (dd, J=8.6, 2.0 Hz, 1 H). $^{31}$P NMR (121 MHz, CDCl$_3$) δ (ppm): 43.64, 43.58. HR-MS (ESI): [M+H]$^+$ Calculated: (C$_{56}$H$_{37}$N$_4$S$_2$P$_2$) 819.1929; Found: 819.1927.
Preparation of N-tert-butyldimethylsilyl-3, 6-dibromocarbazole, 6:

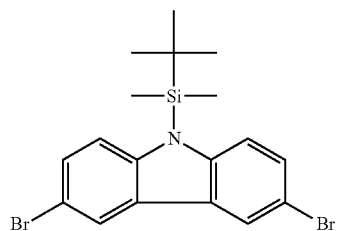 [SMILES: CC(C)(C)[Si](C)(C)n1c2ccc(Br)cc2c2cc(Br)ccc21]

The title compound was prepared from 3,6-dibromocarbazole in the same way of compound 1 according to the published method (Was prepared by the known method (Chem. Mater., 2015, 27, 6535-6542) (White solid. Yield: 95%. $^1$H NMR (400 MHz, CDCl$_3$) δ (ppm): 8.13 (t, J=1.3 Hz, 2 H), 7.48 (d, J=1.3 Hz, 4 H), 1.03 (s, 9 H), 0.76 (s, 6 H). $^{13}$C NMR (100 MHz, CDCl$_3$) δ (ppm): 144.1, 128.7, 127.1, 122.7, 115.6, 112.9, 26.5, 20.6, −1.3.
Preparation of 3, 6-bis(diphenylphosphoryl)carbazole, 7:

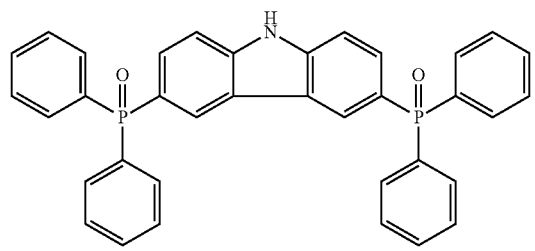 [SMILES: O=P(c1ccccc1)(c1ccccc1)c1ccc2[nH]c3ccc(P(=O)(c4ccccc4)c4ccccc4)cc3c2c1]

The title compound was prepared from compound 6 in the same way of 2 except the equivalences of all reagents are correspondingly doubled.
Preparation of diPPOCzPN, 8:

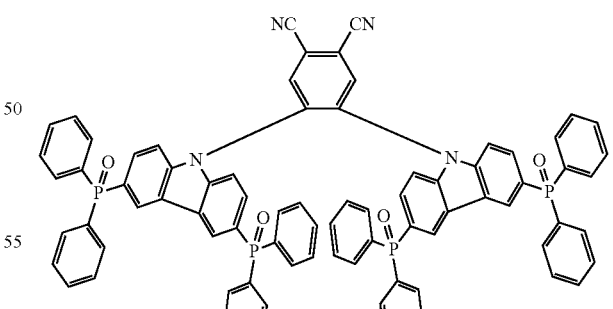

Compound 8 was prepared from 7 in the same way as 4 and 5 were prepared from 2 and 3.

REFERENCES 1. (a) Uoyama, H.; Goushi, K.; Shizu, K.; Nomura, H.; Adachi, C. *Nature* 2012, 492, 234; (b) Nakanotani, H.;

Higuchi, T.; Furukawa, T.; Masui, K.; Morimoto, K.; Numata, M.; Tanaka, H.; Sagara, Y.; Yasuda, T.; Adachi, C. *Nat Commun* 2014, 5, 4016; (c) Zhang, Q.; Li, J.; Shizu, K.; Huang, S.; Hirata, S.; Miyazaki, H.; Adachi, C. *J Am Chem Soc* 2012, 134, 14706; (d) Zhang, Q.; Li, B.; Huang, S.; Nomura, H.; Tanaka, H.; Adachi, C. *Nature Photonics* 2014, 8, 326.

2. Reineke, S. *Nature Photonics* 2014, 8, 269.
3. a) Lee, S. Y.; Yasuda, T.; Yang, Y. S.; Zhang, Q.; Adachi, C. *Angew Chem Int Ed Engl* 2014, 53, 6402; (b) Mehes, G.; Nomura, H.; Zhang, Q.; Nakagawa, T.; Adachi, C. *Angew Chem Int Ed Engl* 2012, 51, 11311.
4. Uoyama, H.; Goushi, K.; Shizu, K.; Nomura, H.; Adachi, C. *Nature* 2012, 492, 234.
5. Crosby, G. A.; Demas, J. N. *J. Phys. Chem.* 1971, 75, 991.
6. Melhuish, W. H. *J. Phys. Chem.* 1961, 65, 229.
7. (a) Zhang, J.; Zhou, L.; Al-Attar, H. A.; Shao, K.; Wang, L.; Zhu, D.; Su, Z.; Bryce, M. R.; Monkman, A. P. *Adv. Fund. Mater.* 2013, 23, 4667; (b) Zheng, Y.; Batsanov, A. S.; Jankus, V.; Dias, F. B.; Bryce, M. R.; Monkman, A. P. *J Org Chem* 2011, 76, 8300; (c) Yu, W.; Huang, G.; Zhang, Y.; Liu, H.; Dong, L.; Yu, X.; Li, Y.; Chang, J. *J Org Chem* 2013, 78, 10337.

The invention claimed is:

1. A TADF compound according to formula I:

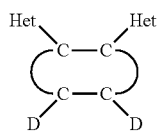

wherein the ring II:

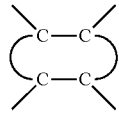

represents an aromatic spacer ring with each Het bonded to adjacent carbon atoms and each moiety D bonded to adjacent carbon atoms, and
    wherein each Het is an aromatic heterocyclic acceptor moiety and each D is a donor moiety
wherein the compound formula I is according to ring III:

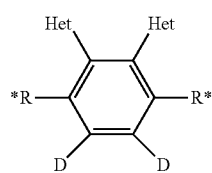

wherein R* is, independently for each occurrence, selected from the group consisting of —H, alkyl, aryl or heteroaryl,
the aromatic heterocyclic acceptor moieties Het are, independently for each occurrence selected from the group consisting of:

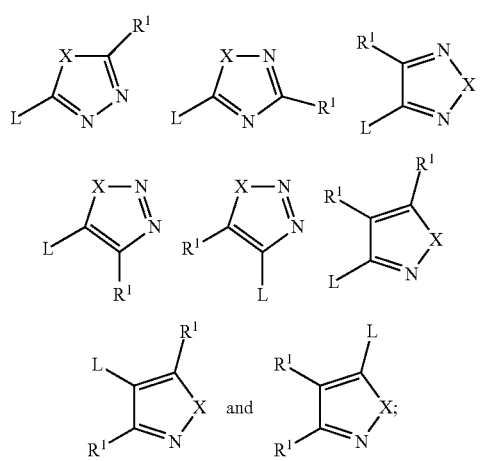

wherein-L represents the bonding position to ring II or III, X represents O, S or $NR^2$ and groups $R^2$ are, independently for each occurrence, selected from the group consisting of —H, substituted or unsubstituted primary, secondary or tertiary alkyl, that may be cyclic and may be unsaturated; substituted or unsubstituted aryl or heteroaryl;

wherein groups $R^1$ are, independently for each occurrence, selected from the group consisting of —H, substituted or unsubstituted primary, secondary or tertiary alkyl, that may be cyclic and may be unsaturated; substituted or unsubstituted aryl or heteroaryl, —$CF_3$, —OMe, —$SF_5$, —$NO_2$, halo, aryl, aryl hydroxy, amino, alkoxy, alkylthio, carboxy, cyano, thio, formyl, ester, acyl, thioacyl, amido, sulfonamido and carbamate, and wherein donor moieties D are independently for each occurrence selected from:

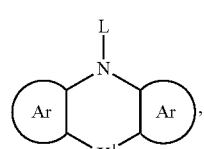

A

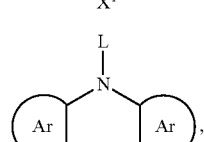

B

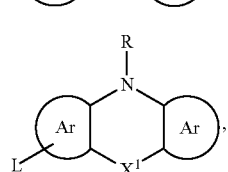

C

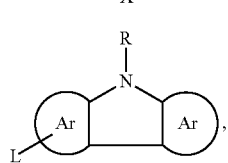

D

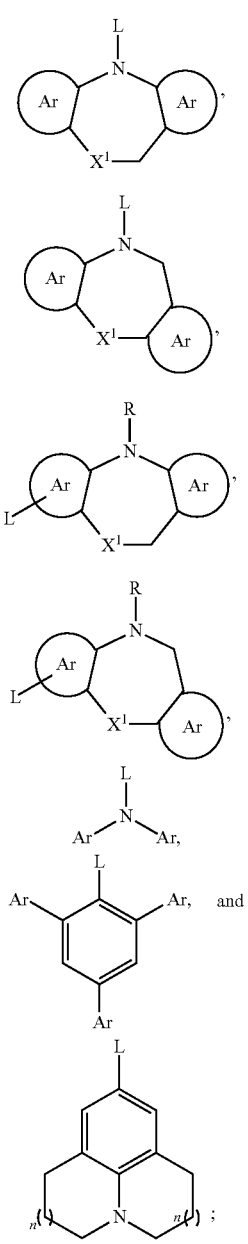

wherein -L represents the bonding position to ring II or III that is para to the nitrogen in structures C, D, G and H;
X¹ is selected from the group consisting of O, S, NR, SiR₂, PR and CR₂, wherein each R is independently selected from the group consisting of —H, alkyl, aryl or heteroaryl;
each Ar is independently for each occurrence selected from the group consisting of substituted or unsubstituted aryl or heteroaryl; and

represents, independently for each occurrence a substituted or unsubstituted aryl or heteroaryl ring fused to the central ring of structures A, B,C, D, E or F, inclusive of a five or a six membered substituted or unsubstituted aryl or heteroaryl ring; and n ( ) indicates the optional presence of saturated —CH₂— groups in the rings annelated to the benzene ring, wherein n is independently for each occurrence, 0, 1, or 2.

2. The TADF compound according to claim 1, wherein the aromatic heterocyclic acceptor moieties Het are 1,3,4 oxadiazoles selected from the group consisting of:

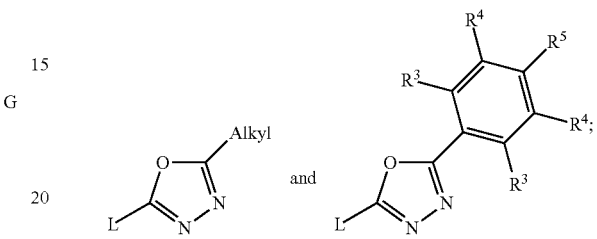

wherein-L represents the bonding position to ring II or III;
—Alkyl represents a substituted or unsubstituted primary, secondary or tertiary alkyl, that may be cyclic and may be unsaturated; and
wherein groups $R^3$, $R^4$ and $R^5$ are, independently for each occurrence selected from the group consisting of:
—H, substituted or unsubstituted primary, secondary or tertiary alkyl, that may be cyclic and may be unsaturated; substituted or unsubstituted aryl or heteroaryl, —CF₃, —OMe, —SF₅, —NO₂, halo, aryl, aryl hydroxy, amino, alkoxy, alkylthio, carboxy, cyano, thio, formyl, ester, acyl, thioacyl, amido, sulfonamido, carbamate, phosphine oxide and phosphine sulphide.

3. The TADF compound according to claim 1, wherein donor moieties D are independently for each occurrence selected from:

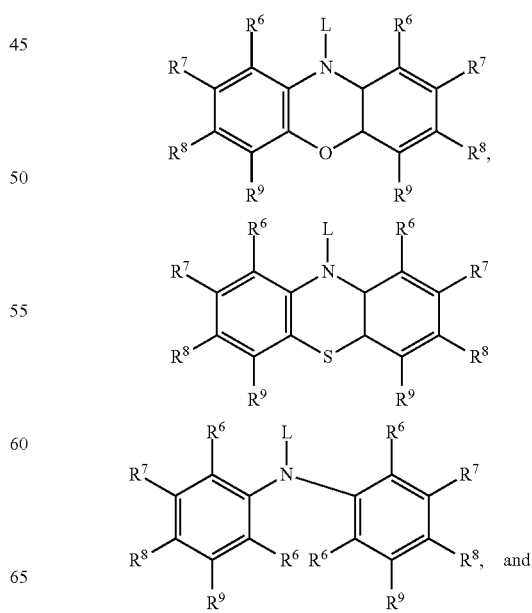

-continued

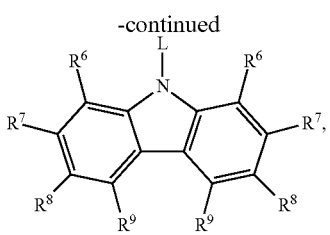

wherein -L represents the bonding position to ring II or III; each group $R^6$, $R^7$, $R^8$ and $R^9$ is, independently for each occurrence, selected from the group consisting of —H, substituted or unsubstituted primary, secondary or tertiary alkyl, that may be cyclic and may be unsaturated; substituted or unsubstituted aryl or heteroaryl, —$CF_3$, —OMe, —$SF_5$, —$NO_2$, halo, aryl, aryl hydroxy, amino, alkoxy, alkylthio, carboxy, cyano, thio, formyl, ester, acyl, thioacyl, amido, sulfonamido, carbamate, phosphine oxide and phosphine sulphide.

4. The TADF compound according to claim 2, selected from the group consisting of:

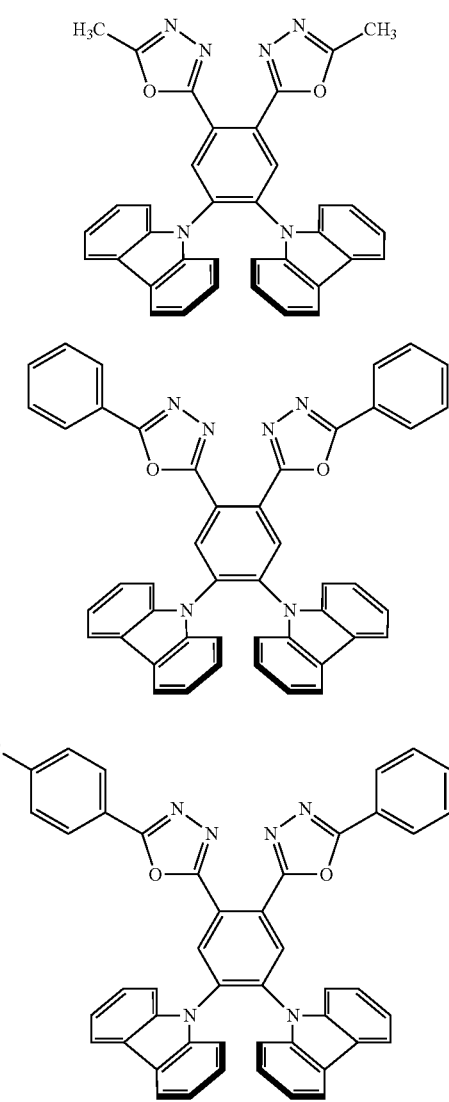

5. A light emitting device comprising a TADF compound according to claim 1.

6. The light emitting device of claim 5, wherein said light emitting device is an OLED.

7. The TADF compound according to claim 1 wherein at least one group $R^1$ is —$NH_2$, —NHR or —$NR_2$; and wherein the substituents R on the nitrogen, when present, are selected from alkyl, aryl or heteroaryl.

8. The TADF compound according to claim 1 wherein at least one donor moiety D has the structure:

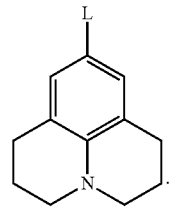

9. The TADF compound according to claim 1 wherein at least one —Ar or

where present, includes at least one phosphine oxide or phosphine sulphide substituent.

10. The TADF compound according to claim 3 wherein one or more of groups $R^6$, $R^7$, $R^8$ and $R^9$ is amino and is —$NH_2$, —NHR or —$NR_2$; and wherein the substituents R on the nitrogen, when present, are selected from alkyl, aryl or heteroaryl.

11. The TADF compound according to claim 3 wherein one or more of groups $R^6$, $R^7$, $R^8$ and $R^9$ are selected from the group consisting of:

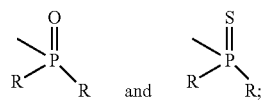

wherein the substituents R on the phosphorus are substituted or unsubstituted alkyl, aryl or heteroaryl.

12. The TADF compound according to 11 wherein one or more of groups $R^6$, $R^7$, $R^8$ and $R^9$ are selected from the group consisting of:

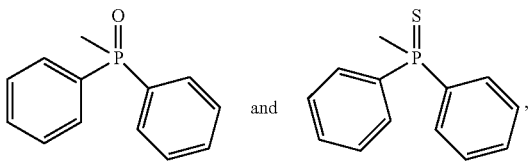

optionally wherein one or both of the phenyl groups on the phosphorous are substituted.

13. The TADF compound according to 11 wherein one or both of groups $R^8$ are selected from the group consisting of:

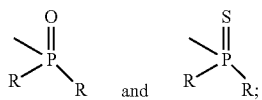
wherein the substituents R on the phosphorus are substituted or unsubstituted alkyl, aryl or heteroaryl.
14. The TADF compound according to claim 4, wherein said compound is:
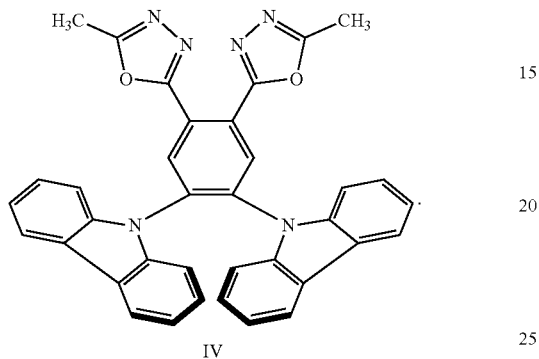
IV
* * * * *